US010847248B2

(12) United States Patent
Bustamante et al.

(10) Patent No.: US 10,847,248 B2
(45) Date of Patent: Nov. 24, 2020

(54) TECHNIQUES FOR DETERMINING HAPLOTYPE BY POPULATION GENOTYPE AND SEQUENCE DATA

(71) Applicants: Carlos D. Bustamante, Emerald Hills, CA (US); Fouad Zakharia, San Francisco, CA (US)

(72) Inventors: Carlos D. Bustamante, Emerald Hills, CA (US); Fouad Zakharia, San Francisco, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 476 days.

(21) Appl. No.: 13/964,758

(22) Filed: Aug. 12, 2013

(65) Prior Publication Data
US 2014/0045705 A1   Feb. 13, 2014

Related U.S. Application Data

(60) Provisional application No. 61/681,682, filed on Aug. 10, 2012.

(51) Int. Cl.
G16B 20/00   (2019.01)
G16B 30/00   (2019.01)

(52) U.S. Cl.
CPC .............. *G16B 20/00* (2019.02); *G16B 30/00* (2019.02)

(58) Field of Classification Search
None
See application file for complete search history.

(56) References Cited

PUBLICATIONS

Byung-Jun Yoon, Hidden Markov Models and their Applications in Biological Sequence Analysis, Curr Genomics. Sep. 2009; 10(6): 402-415, doi: 10.2174/138920209789177575.*
V Bansal et al., "An MCMC algorithm for haplotype assembly from whole-genome sequence data", "Genome Research", 2008, pp. 1336-1346, vol. 18, No. 8, Publisher: Cold Spring Harbor Laboratory Press, Published in: http://www.ncbi.nlm.nih.gov/pubmed/18676820.
V Bansal et al., "HapCUT: an efficient and accurate algorithm for the haplotype assembly problem", "Bioinformatics", 2008, pp. i153-i159, vol. 24, No. 16, Publisher: Oxford University Press, Published in: http://www.ncbi.nlm.nih.gov/pubmed/18689818.
D Bentley et al., "Accurate whole human genome sequencing using reversible terminator chemistry", "Nature", 2008, pp. 53-59, vol. 456, No. 7218, Publisher: Nature Publishing Group, Published in: http://www.ncbi.nlm.nih.gov/pubmed/18987734.
S Browning et al., "Rapid and accurate haplotype phasing and missing-data inference for whole-genome association studies by use of localized", "The American Journal of Human Genetics", 2007, pp. 1084-1097, vol. 81, No. 5, Publisher: Cell Press, Published in: http://www.ncbi.nlm.nih.gov/pubmed/17924348.
O Delaneau et al., "A linear complexity phasing method for thousands of genomes", "Nature Methods", 2011, pp. 179-181, vol. 9, No. 2, Publisher: Nature Publishing Group, Published in: http://www.ncbi.nlm.nih.gov/pubmed/22138821.
F Dewey et al., "Phased Whole-Genome Genetic Risk in a Family Quartet Using a Major Allele Reference Sequence", "PLOS Genetics", 2011, p. e1002280 [15 pages], vol. 7, No. 9, Publisher: PLOS, Published in: http://www.plosgenetics.org/article/info%3Adoi%2F10.1371%2Fjournal.pgen.1002280.
H Fan et al., "Whole-genome molecular haplotyping of single cells", "Nature Biotechnology", 2011, pp. 51-57, vol. 29, No. 1, Publisher: Nature Publishing Group, Published in: http://www.ncbi.nlm.nih.gov/pubmed/21170043.
J Kitzman et al., "Haplotype-resolved genome sequencing of a Gujarati Indian individual", "Nature Biotechnology", 2011, pp. 59-63, vol. 29, No. 1, Publisher: Nature Publishing Group, Published in: http://www.nature.com/nbt/journal/v29/n1/abs/nbt.1740.html.
N Li et al., "Modeling Linkage Disequilibrium and Identifying Recombination Hotspots Using Single-Nucleotide Polymorphism Data", "Genes, Genomes, Genetics", 2003, pp. 2213-2233, vol. 165, No. 4, Publisher: Genetics Society of America, Published in: http://www.genetics.org/content/165/4/2213.long.
Q Long et al., "HI: haplotype improver using paired-end short reads", "Bioinformatics", 2009, pp. 2436-2437, vol. 25, No. 18, Publisher: Oxford University Press, Published in: http://www.ncbi.nlm.nih.gov/pubmed/19570807.
K McKernan et al., "Sequence and structural variation in a human genome uncovered by short-read, massively parallel ligation sequencing usin", "Genome Research", 2009, pp. 1527-1541, vol. 19, No. 9, Publisher: Cold Spring Harbor Laboratory Press, Published in: http://www.ncbi.nlm.nih.gov/pubmed/19546169.

(Continued)

*Primary Examiner* — Joseph Woitach
(74) *Attorney, Agent, or Firm* — Wolter Van Dyke Davis, PLLC; Eugene J. Molinelli

(57) ABSTRACT

A novel phasing algorithm harnesses sequencing read information from next generation sequencing technologies to guide and improve local haplotype reconstruction from genotypes. Techniques include determining correlated occurrences of single nucleotide polymorphisms (SNPs) in genes of a population of individuals. A plurality of sequences of nucleotide bases in one or more individuals from the populations of individuals is determined based on ultra-high throughput sequencing of a sample from the one or more individuals. Haplotypes included in the population of individuals are determined based on both the correlated occurrences and the plurality of sequences. The inclusion of paired end read data is especially advantageous for the phasing of rare variants, including singletons.

27 Claims, 12 Drawing Sheets

(56) References Cited

PUBLICATIONS

P Scheet et al., "A fast and flexible statistical model for large-scale population genotype data: applications to inferring missing genoty", "The American Journal of Human Genetics", 2006, pp. 629-644, vol. 78, No. 4, Publisher: Cell Press, Published in: http://www.ncbi.nlm.nih.gov/pubmed/16532393.

* cited by examiner

FIG. 1D

| SNP POSITION | SNP VALUES IN GENOTYPE DATA | SNP POSITION | SNP VALUES |
|---|---|---|---|
| 1 | 0,1 | 20 | 0 |
| 2 | 0,1 | 21 | 1 |
| 3 | 0,1 | 22 | 0 |
| 4 | 0,1 | 23 | 0,1 |
| 5 | 1 | 24 | 0,1 |
| 6 | 1 | 25 | 1 |
| 7 | 0,1 | 26 | 1 |
| 8 | 0,1 | 27 | 0,1 |
| 9 | 0,1 | 28 | 1 |
| 10 | 0,1 | 29 | 0,1 |
| 11 | 0,1 | 30 | 0,1 |
| 12 | 1 | 31 | 0,1 |
| 13 | 0 | 32 | 1 |
| 14 | 1 | 33 | 0,1 |
| 15 | 0 | 34 | 0,1 |
| 16 | 1 | 35 | 1 |
| 17 | 0,1 | 36 | 0,1 |
| 18 | 0,1 | 37 | 0,1 |
| 19 | 0,1 | 38 | 0,1 |

FIG. 3C

| SNP POSITION | SNP VALUES IN SEQUENCE DATA | SNP POSITION | SNP VALUES |
|---|---|---|---|
| 1 |  | 20 |  |
| 2 |  | 21 |  |
| 3 |  | 22 |  |
| 4 |  | 23 |  |
| 5 |  | 24 |  |
| 6 | 1 | 25 |  |
| 7 | 0 | 26 |  |
| 8 | 0 | 27 |  |
| 9 |  | 28 |  |
| 10 |  | 29 |  |
| 11 |  | 30 |  |
| 12 | 1 | 31 |  |
| 13 | 0 | 32 |  |
| 14 |  | 33 |  |
| 15 |  | 34 |  |
| 16 |  | 35 |  |
| 17 |  | 36 |  |
| 18 |  | 37 |  |
| 19 |  | 38 |  |

TECHNIQUES FOR DETERMINING HAPLOTYPE BY POPULATION GENOTYPE AND SEQUENCE DATA

BACKGROUND OF THE INVENTION

Definitions Table

| | |
|---|---|
| allele | One of two or more forms of a gene or a genetic locus (generally a group of genes) on a single chromosome. |
| ambiguous marker | A marker associated with heterozygous alleles or missing in a particular individual. |
| chromosome | A single piece of coiled DNA containing many genes, regulatory elements and other nucleotide sequences also containing DNA-bound proteins, which serve to package the DNA and control its functions. |
| diploid | Two homologous copies of each chromosome, with genes for the same characteristics at corresponding positions (loci), usually one from the mother and one from the father. |
| gene | A segment of DNA involved in producing a polypeptide chain. Specifically, a gene includes, without limitation, regions preceding and following the coding region, such as the promoter and 3'-untranslated region, respectively, as well as intervening sequences (introns) between individual coding segments (exons). |
| genotype | The genetic composition of an organism. |
| haplotype | 1 - A combination of alleles (DNA sequences) at adjacent locations (loci) on the chromosome that are transmitted together. 2 - A set of single-nucleotide polymorphisms (SNPs) on a single chromosome of a chromosome pair that are statistically associated. |
| heterozygous | A diploid organism is heterozygous at a gene locus when its cells contain two different alleles of a gene. Heterozygous genotypes are represented by a capital letter (representing the dominant allele) and a lowercase letter (representing the recessive allele), such as "Rr" or "Ss". The capital letter is usually written first. |
| LD | Linkage disequilibrium, the non-random association of alleles at two or more loci, not necessarily on the same chromosome. |
| marker | A gene or unique DNA sequence with a known location on a chromosome that can be used to determine the chromosome location of an arbitrary sequenced portion of DNA. |
| nucleic acid | A molecule comprising a sequence of one or more repeating chemical units known as "nucleotides" or "bases" or "base pairs" (bp). There are four bases in deoxyribonucleic acid (DNA): adenine, thymine, cytosine, and guanine, represented by the letters A, T, C and G, respectively. In Ribonucleic acid (RNA) the base uracil (U) replaces the base thymine (T). |
| reference panel | A full set of haplotypes represented in a population, each haplotype represented by a set of SNPs at known positions relative to a set of markers along each chromosome. |
| phasing | Determining which alleles (indicated by the variant SNPs) exist together on the same chromosome, i.e., belong to the same haplotype. |
| protein | A generic term referring to native protein, fragments, peptides, or analogs of a polypeptide sequence. Synonyms used herein include "polypeptide." Hence, native protein, fragments, and analogs are species of a polypeptide genus. |
| sample | includes any biological specimen obtained from a subject |
| SNP | Single-nucleotide polymorphism, a DNA sequence variation occurring when a single nucleotide in the genome (or other shared sequence) differs between members of a biological species or paired chromosomes in an individual. The vast majority of polymorphic sites are bi-allelic, meaning that no more than two possible distinct alleles can be observed at these sites. As used herein, a 0 indicates one nucleotide at the position of the SNP and a 1 indicates a different nucleotide. |
| subject | An organism that is an object of a method or material, including mammals, e.g., humans, dogs, cows, horses, kangaroos, pigs, sheep, goats, cats, mice, rabbits, rats, and transgenic non-human animals as well as plants and protists. Synonyms used herein include "patient" and "animal". |
| treating | Taking steps to obtain beneficial or desired results, including clinical results, such as alleviating or ameliorating one or more symptoms of a disease; diminishing the extent of disease; delaying or slowing disease progression; ameliorating and palliating or stabilizing a metric (statistic) of disease. "Treatment" refers to the steps taken. |

Most humans carry 2 copies of every chromosome in their genome—one inherited from the mother, the other from the father. Current genotyping and sequencing technologies have empowered us with the ability to rapidly and inexpensively discover the genotypes of an individual at a large number of sites in the genome (based on the SNPs in the vicinity of various markers). However, they do not provide us with a direct way of knowing the phase of these individuals: we cannot immediately determine which alleles were inherited together from one parent or the other. This task is made more difficult by the fact that most human genetic studies have sampled unrelated individuals, so that the genotypes of their parents are unknown. Related individuals share long haplotypes, which can be used to perform long-range phasing. Unrelated individuals also share haplotypes, but these are generally shorter and more difficult to infer.

FIG. 1A is a block diagram that illustrates example haplotypes in related individuals in a related population 100. For simplicity, the process is shown for three generations in which no admixture events occur. In this simplified illustration, a child chromosome pair 110 is made up a first chromosome entirely of haplotype 151 inherited from one parent and a second chromosome entirely of haplotype 152 inherited from the other parent. Each haplotype is shown as unique because each consists of a different set of SNP values distributed at known SNP locations through the chromosome. In ethnically similar ancestors, the two haplotypes have very many similar SNPs, even though the fill patterns used to distinguish the haplotypes in FIG. 1A are very different.

Going up a generation, one parent chromosome pair 121 includes the haplotype 151 inherited by the child chromosome pair 110 and a second different haplotype 153 that was not inherited; while, the other parent chromosome pair 122 includes the haplotype 152 inherited by the child chromosome pair 110 and yet another different haplotype 154 that was not inherited. At the next ancestral generation, a first grandparent chromosome pair 131 includes the haplotype 151 inherited by parent chromosome pair 121 and a different haplotype 155 that was not inherited. The other grandparent chromosome pair 132 includes the haplotype 153 inherited by parent chromosome pair 121 and a different haplotype 157 that was not inherited. Similarly, a third grandparent chromosome pair 133 includes the haplotype 152 inherited by parent chromosome pair 122 and a different haplotype 156 that was not inherited. The fourth grandparent chromosome pair 134 includes the haplotype 154 inherited by parent chromosome pair 122 and a different haplotype 158 that was not inherited. In this related population 100, there are 8 different haplotypes (252 through 158), among which haplotype 151 and haplotype 152 are each repeated three times, and haplotype 153 and haplotype 154 are each repeated twice.

In some recombination events, a segment of a chromosome is replaced by the corresponding segment of the paired chromosome during inheritance. This is depicted in FIG. 1B, which is a block diagram that illustrates example haplotypes in related individuals in a second related population 106. In this example, the chromosome inherited from parent chromosome pair 121 includes a portion of haplotype 153 replacing corresponding portion of haplotype 151 and two portions of haplotype 151.

After many generations, an individual may have multiple haplotypes on each chromosome as depicted in FIG. 1C. FIG. 1C is a block diagram that illustrates an example chromosome pair 117 in which each chromosome includes multiple portions of different haplotypes. A change from one haplotype to anther is called a haplotype transition and indicated in FIG. 1C by fill pattern changes, e.g., at haplotype transitions 175 on one chromosome. For a simplified illustration, it is assumed that the chromosome includes 38 known SNP positions relative to markers for different locations in each chromosome, corresponding to a similar number of alleles. Thus each chromosome has a set of 38 SNP values (0 for one nucleotide at each SNP position and 1 for a different nucleotide). SNP set 171 gives example SNP values for one chromosome, with different lines corresponding to different haplotype segments. SNP set 172 gives example SNP values for the other chromosome, with different lines corresponding to different haplotype segments on the other chromosome. A computational segment length 180 is indicated as described in a later section with respect to the detailed description of embodiments of the invention.

Genotype information gives the occurrence of the alleles, e.g., the paired values for the SNPs, but does not establish which were inherited together, e.g., does not establish the membership in the different SNP sets 171 and 172 for the different chromosomes. FIG. 1D is a table that lists example genotype data produced from the chromosome pair depicted in FIG. 1C. As listed in FIG. 1D, genotype information indicates the occurrence of both SNP values $\{0,1\}$ at the first SNP position but does not indicate which chromosome provided the 0 and which provided the 1. Similarly, genotype information indicates the occurrence of both SNP values $\{0,1\}$ at the second SNP position but does not indicate which chromosome provided the 0 and which provided the 1, or even whether the two 0 values at the two successive SNP positions came from the same chromosome or from different chromosomes. The SNP positions with multiple values in the table of FIG. 1D represent heterozygous alleles in the individual, e.g., where different alleles are inherited from the different parents, and the markers associated with each SNP are called ambiguous markers, because it is not clear which parent the marker and associated SNPS came from. So markers associated with SNP positions 1 to 4 are ambiguous. Markers associated with SNP positions with a single value are not ambiguous, because it is known that the listed value appeared on the chromosomes received from both parents.

Haplotype information is critical to many analyses in population genetics. Many methods of demographic inference rely on haplotype diversity to gain insight into the history of a population, such as possible bottlenecks, range expansions, and strong selection events. In admixed populations, with multiple chromosomal segments inherited from corresponding ancestral populations on a single chromosome, phasing can be coupled with local ancestry de-convolution to yield estimates of ancestry track length in every individual; these estimates in turn can be used to make inferences on the admixture history of these populations, such as the time and the dynamics of the admixture event.

A number of statistical methods have been developed over the years to phase unrelated individuals in the absence of parent information, e.g., to determine the values in each SNP set 171 and 172 or haplotype transitions (e.g., transitions 175) based on the 38 values in each SNP set (e.g., SNP set 172). The most advanced of these methods generally yield comparable accuracies in their reconstruction of the haplotypes, and obtaining better performance has become quite challenging using genotype information alone.

Poorly reconstructed haplotypes can dramatically impair subsequent statistical analyses on the data. For instance, genetic association studies relying on haplotype associations to uncover the molecular basis of disease may be underpowered, or suffer from a higher false positive rate. Demographic analyses on a population may yield inaccurate or biased estimates of population growth parameters. Finally, studies on admixed populations may suffer from a higher error rate in local ancestry inference.

SUMMARY OF THE INVENTION

Applicants have recognized that the advent of next generation sequencing technologies offers the opportunity to obtain better phasing. Briefly, these technologies rely on a "shotgun-sequencing" approach, whereby hundreds of millions of short (50-200 bp) DNA-based reads are used to tile the entirety of a genome, based on overlapping sequences and markers. Whenever these reads span two or more heterozygous sites, they effectively inform about the phase of those sites in that individual. Techniques are provided to integrate this sequence read information with existing phasing approaches to achieve superior accuracy.

An advantage of some embodiments of these phasing techniques over existing algorithms lies in the fact that they exploit information from novel sequencing technologies to improve haplotype inference, whereas current state of the art methods restrict themselves to genotype data. Depending on the population, sample size, and the technology used to supplement the phasing, some embodiments have been shown to yield substantially lower error rates compared to extant algorithms. A second advantage, in some embodiments, pertains to the phasing of rare variants. Sites of rare variants in the genome are particularly challenging to phase using existing methods, but can readily be phased if they happen to be linked to less rare variants by sequencing reads.

While some embodiments are designed to take advantage of sequencing reads, other embodiments are generalized to benefit from any other external source of local phasing information. For example, when available, some embodiments take advantage of smaller sample family data (such as trio data, comprising genotypes of two parents and a child, on a lower density genotyping chip) to significantly improve haplotype reconstruction.

In various embodiments, these phasing techniques are applied in any study relying on the generation of high quality haplotypes; in demographic inferences for a population; in Identity by Descent (IBD) studies; in cryptic relatedness studies; in phased local ancestry deconvolution in admixed populations; and haplotype-based association studies, such as those conducted in medical genetic studies.

In a first set of embodiments, a method includes determining correlated occurrences of single nucleotide polymorphisms (SNPs) in genes of a population of individuals. The method also includes determining a plurality of sequences of nucleotide bases in one or more individuals from the populations of individuals based on sequencing of a sample from the one or more individuals. The method still further includes determining, on a processor, haplotypes included in the population of individuals based on both the correlated occurrences and the plurality of sequences. In some embodiments of this set, the method also includes determining haplotypes included in a chromosome of an individual based, at least in part, on haplotypes included in the population and one or more sequences of nucleotide bases for the individual. In some of the embodiments of the first set, determining the plurality of sequences of nucleotide bases in the one or more individuals from the populations of individuals is based on ultra-high throughput sequencing of the sample from the one or more individuals.

In other sets of embodiments, a computer-readable medium or a system is configured to perform one or more of the steps of the above methods.

Still other aspects, features, and advantages of the invention are readily apparent from the following detailed description, simply by illustrating a number of particular embodiments and implementations, including the best mode contemplated for carrying out the invention. The invention is also capable of other and different embodiments, and its several details can be modified in various obvious respects, all without departing from the spirit and scope of the invention. Accordingly, the drawings and description are to be regarded as illustrative in nature, and not as restrictive.

BRIEF DESCRIPTION OF THE DRAWINGS

The present invention is illustrated by way of example, and not by way of limitation, in the figures of the accompanying drawings and in which like reference numerals refer to similar elements and in which:

FIG. 1D is a table that lists example genotype data produced from the chromosome pair depicted in FIG. 1C;

FIG. 3C is a table that illustrates example values for SNPS physically linked by sequence data, according to an embodiment;

DETAILED DESCRIPTION

Figure 1A:
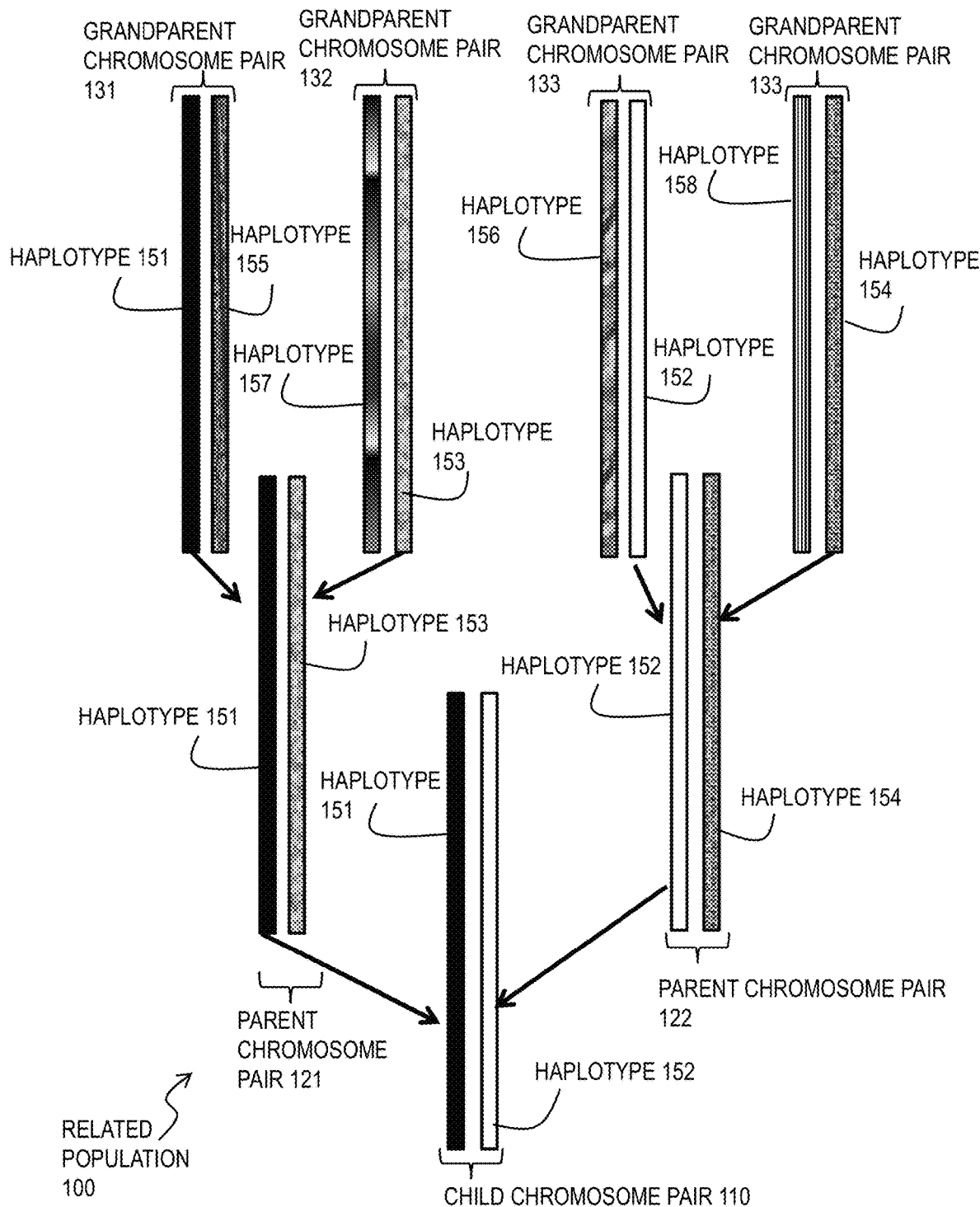
FIG. 1A is a block diagram that illustrates example haplotypes in related individuals in a related population.
Figure 1B:
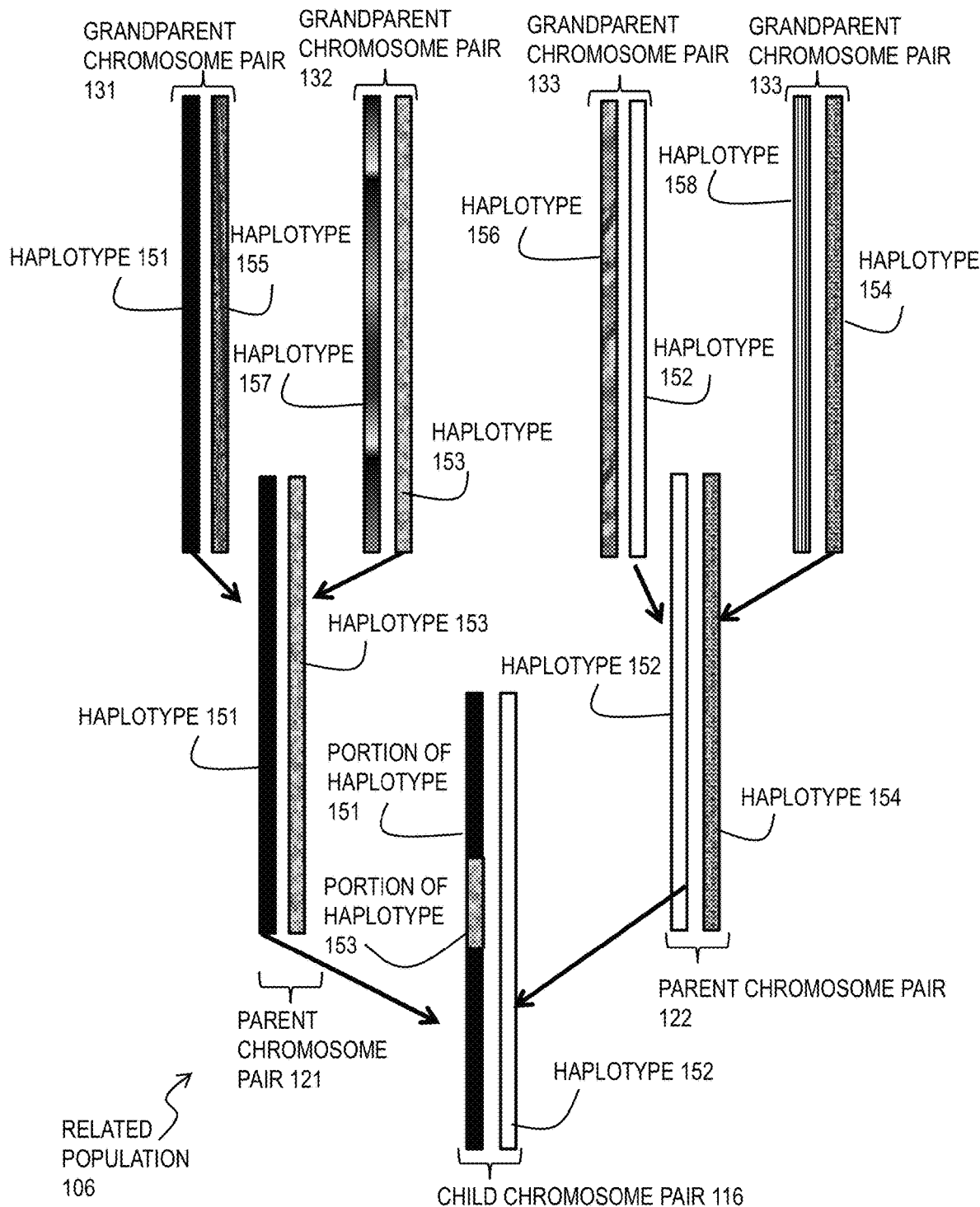
FIG. 1B, which is a block diagram that illustrates example haplotypes in related individuals in a second related population.

A method and apparatus are described for determining haplotype by population genotype and sequence data. In the following description, for the purposes of explanation, numerous specific details are set forth in order to provide a thorough understanding of the present invention. It will be apparent, however, to one skilled in the art that the present invention may be practiced without these specific details. In other instances, well-known structures and devices are shown in block diagram form in order to avoid unnecessarily obscuring the present invention. In the following description many references are cited. The entire contents of each reference cited below is hereby incorporated by reference as if fully recited herein, except for terminology that is inconsistent with the terminology used herein.

To date, several phasing algorithms have been developed to perform phasing on large-scale datasets, and these generally appear to yield similar results on commercial genotype arrays (up to 1 million SNPs). A genotype array indicates which individual SNPs occur in a sample by providing binding sites for sequences in the vicinity of these SNPs, but, in general, do not include binding sites for successive SNPs.

Some embodiments of the invention are described below in the context of particular modifications to a particular extant phasing model, ShapeIT. However, the invention is not limited to this context. In other embodiments similar modifications are made to the same or different genotype phasing models.

Extant phasing methods include: (1) ShapeIT: described in O. Delaneau, J. Marchini, J. F. Zagury, "A linear complexity phasing method for thousands of genomes," *Nature Methods* v9 n2, pp 179-81, 2011; (2) fastPHASE: described in P. Scheet and M. Stephens, "A fast and flexible statistical model for large-scale population genotype data: Applications to inferring missing genotypes and haplotypic phase," *American Journal of Human Genetics* v78 n4, pp 629-44, 2006; (3) HI: described in Q. Long, D. MacArthur, Z. Ning, and C. Tyler-Smith, "HI: Haplotype improver using paired-end short reads," *Bioinformatics* v25 n18, pp 2436-7, 2009; (4) Beagle: S. R. Browning and B. L. Browning, described in "Rapid and accurate haplotype phasing and missing data inference for whole genome association studies using localized haplotype clustering," *American Journal of Human Genetics* v81, pp 1084-97, 2007; and (5) West Quartet: described in F. E. Dewey, R. Chen, S. P. Cordero, K. E. Ormond, C. Caleshu, et al., "Phased Whole-Genome Genetic Risk in a Family Quartet Using a Major Allele Reference Sequence," *PLOS Genetics* v7 n9, 2011: e1002280. doi:10.1371/journal.pgen.1002280.

Statistical methods relying on linkage disequilibrium (LD) patterns can be used to infer short range haplotypes (SNPs separated on the order of about 50,000 to about 100,000 bases) but provide little to no information on longer range phasing. To date, several algorithms, such as those listed above, have been developed to perform phasing on large-scale datasets, and these generally appear to yield similar results on commercial arrays (providing genotypes for up to 1 million SNPs), with an average 5% to 7% error rate between adjacent heterozygous loci for sufficiently large sample sizes. Errors refers to misidentifying the correct relationship among the two pairs of alleles. Consider heterozygous locus 1 with alleles "A" and "a" and heterozygous locus 2 with alleles "B" and "b". There are four possible haplotypes AB, aB, Ab, and ab. When one uses population phasing, one gets an estimate of the frequencies of the four. It is most likely that one pair includes both major haplotypes, so either AB+ab or Ab+aB has high frequency, with the other haplotypes as rare recombinants.

According to various embodiments described herein, high coverage afforded by ultra-high throughput sequencing (UHTS) technologies is exploited to reduce those error rates. Such UHTS include Whole Genome Sequencing (WGS) and Genotyping by Sequencing (GBS). Current algorithms are likely to experience mixed results with such datasets. On the one hand, increased marker density provided by such methods should lead to the discovery of markers that are on average more tightly linked to one another than those found on ordinary SNP array chips. On the other hand, many of these markers are expected to be rare variants, and these are not easily tagged by (e.g., associated with) common alleles. These can pose a substantial challenge to phasing algorithms, since in those cases the minor allele will only be represented in a handful of individuals, reducing statistical power.

The gradual shift from SNP array chips to sequencing has spurred a considerable interest in methods designed to physically phase haplotypes from sequencing data. Several statistical algorithms have been developed towards the haplotype assembly problem, whereby haplotypes are directly constructed from the DNA fragments used to assemble the genome. These can be fairly straightforward methods, handling gapped fragments and sequencing errors in a primarily heuristic fashion; others are more statistically involved. For example, HASH (V. Bansal, A. L. Halpern, N. Axelrod, V. Bafna, "An MCMC algorithm for haplotype assembly from whole-genome sequence data," *Genome Research* v18 n8, pp 1336-46, 2008) uses a Markov Chain Monte Carlo (MCMC) method, which samples from probability distributions based on constructing a Markov chain that has the desired distribution as its equilibrium distribution. As another example, HapCUT (V. Bansal, V. Bafna, "HapCUT: an efficient and accurate algorithm for the haplotype assembly problem," *Bioinformatics* v24 n16, ppi153-9, 2008) is a max-cut based algorithm for haplotype assembly that uses the mix of sequenced fragments from the two chromosomes of an individual. The algorithm was developed at UC San Diego by Vikas Bansal, Ph.D., for phasing Craig Venter, Ph.D.'s genome, which was deciphered by Sanger sequencing technology and which relies on a combinatorial graph-cutting algorithm. In all of these cases, the haplotype reconstruction is done one individual at a time, and is done independently of the population under study. Thus, the success of these algorithms is critically dependent on the sequencing depth (number of base pairs sequenced together) and the length of the fragments used to tile the target genome—otherwise, only small haplotype blocks can be reconstructed from the data.

Molecular phasing algorithms are designed to incorporate known physical links between heterozygous SNPs to solve the phasing problem. A known physical link means that there is a physical DNA molecule that has been sequenced which supports the association among locus 1 and locus 2. Specifically, when "paired end" sequencing is performed, a sequence from both ends of an ~300-400 base pair molecule is obtained. If SNP 1 is on one end of the molecule (say position 50) with possible variants "A" (0) and "G" (1) and SNP 2 is on the other end of the molecule (say position 325) with possible variants "C" (0) and "T" (1) and a measured DNA sequence reads "A" at position 50 and "C" at position 325 (0,0), there is physical evidence that the correct phasing is "A-C" (0-0).

In addition to these molecular phasing algorithms, a number of technologies have recently been developed to sequence each chromosome in a cell separately. In a sense, these techniques seek to provide a cheaper alternative to sperm typing, in which individual haploid gametes are collected and sequenced. For instance, Kitzman et al. (J. O. Kitzman, A. P. Mackenzie, A. Adey, J. B. Hiatt, R. P. Patwardhan, P. H. Sudmant, S. B. Ng, C. Alkan, R. Qiu, E. E. Eichler, and J. Shendure, "Haplotype-resolved genome sequencing of a Gujarati Indian individual," *Nature Biotechnology* v29 n1, pp 59-63, 2011) successfully generated the phased genome of a Gujarati individual through the use of fosmid libraries. Fosmids can hold DNA inserts of up to 40 kb in size. A fosmid library is prepared by extracting the genomic DNA from the target organism and cloning it into the fosmid vector for a bacterial host, like *Escherichia coli* (*E. coli*). The ligation mix is then packaged into phage particles and the DNA is transfected into the bacterial host. Bacterial clones propagate the fosmid library. The low copy number offers higher stability than vectors with relatively higher copy numbers, including cosmids. As another example, Fan et al. (H. C. Fan, J. Wang, A. Potanina, and S.

R. Quake, "Whole-genome molecular haplotyping of single cells," *Nature Biotechnology* v29 n1, pp 51-7, 2011) developed an assay capable of directly haplotyping the genome of single cells. While these technologies have been shown to reconstruct high-quality haplotypes from diploid cells, they remain comparatively low-throughput, both in terms of cost and running time.

An object of some embodiments of the present techniques is to combine population-level LD information with the read data from UHTS to achieve higher accuracy in haplotype reconstruction. Present technologies generate hundreds of millions of short (30-100 bp) reads to cover the target genomes. Some methods support paired end reads, including SOLiD (D. R. Bentley, S. Balasubramanian, H. P. Swerdlow, G. P. Smith, J. Milton, C. G. Brown, K. P. Hall, D. J. Evers, C. L. Barnes, H. R. Bignell, et al., "Accurate whole human genome sequencing using reversible terminator chemistry," *Nature* v456 n7218, pp 53-9, 2008) and Illumina (K. J. McKernan, H. E. Peckham, G. L. Costa, S. F. McLaughlin, Y. Fu, E. F. Tsung, C. R. Clouser, C. Duncan, J. K. Ichikawa, C. C. Lee, et al., "Sequence and structural variation in a human genome uncovered by short-read, massively parallel ligation sequencing using two-base encoding, "*Genome Research* v19 n9, pp 1527-41, 2009). Paired-end tags (PET) are the short sequences at the 5' and 3' ends of the DNA fragment of interest, which can be a piece of genomic DNA or cDNA. These short sequences are called tags or signatures because, in theory, they should contain enough sequence information to be uniquely mapped to the genome and thus represent the whole DNA fragment of interest. It was shown conceptually that 13 bp are sufficient to map tags uniquely. However, longer sequences are more practical for mapping reads uniquely. Methods using paired end reads thus link nearby regions of the genome (generally 0.3 to 2 kilobases, kb, apart, 1 kb=$10^3$ bases). By default, any read spanning two or more heterozygous sites (e.g., heterozygous SNP loci for an individual) holds the key to their phasing configuration. Given the massively parallel nature of these technologies, one can expect that a considerable number of sequencing reads will be informative with respect to phase (e.g., include two or more SNP loci). Thus, incorporating the phasing information from the reads into current population-based algorithms is likely to improve the quality of the inferred haplotypes. Embodiments of the current invention have established methods to do so.

The incorporation of read data into a conventional phasing algorithm (e.g., ShapeIT) is not straightforward. All of the extant statistical phasing methods rely on a Hidden Markov Model (HMM) framework for phasing. This implies that each of these algorithms assumes that the haplotype affiliation of a given marker for an SNP is solely dependent on that of the previous marker in the chain. This assumption is primarily motivated by computational reasons: by focusing solely on the previous marker, one does not need to account for the phase of markers further back along the chromosome; enumerating every possible phase configuration along the genome would rapidly become computationally intractable. The HMM outputs a posterior distribution of haplotypes. The posterior distributions comprise a table with each possible haplotype as a row, and with probability of that being the correct haplotype, conditional on the SNP genotypes, as a column. That is, the haplotypes in the table are the possible solutions and the posterior probability gives the probability that a given solution is correct. For example, for two loci with alleles A/a, B/b in an individual who is, by definition, heterozygous at those positions, the output might be:

| | |
|---|---|
| A-B/a-b | 98% |
| A-b/a-B | 2% |

For three loci with alleles, A/a, B/b, C/c where the third SNP is 3' of the other two for an individual which is heterozygous at those positions, the possible solutions and probabilities might be:

| | |
|---|---|
| A-B-C/a-b-c | 90% |
| A-b-C/a-B-c | 1% |
| A-B-c/a-b-C | 8% |
| A-b-c/a-B-C | 1%. |

The incorporation of read data poses a big challenge to the Markov models. With current technologies allowing for increasingly large insert sizes between paired reads, it is very common for SNPs to be linked to markers that are not immediately adjacent to them. Since markers can be linked to multiple SNPs both preceding and following them along the chromosome, the naïve approach of adapting these HMM models into higher order Markov chains would be difficult to generalize to an arbitrary number of read links, and would quickly become computationally infeasible. Furthermore, none of these statistical methods offers a straightforward way of allowing sequence data from one individual to improve the phasing of genotypes from the other individuals in the population.

To account for these challenges, a method was developed that does not directly modify the HMM used in various phasing algorithms, such as in ShapeIT. Instead, the read data is introduced at a diplotype simulation method, such as in a Gibbs sampling stage used in ShapeIT among others. In these simulation methods, multiple haplotypes are sampled from the posterior distribution of the HMM. The distribution of the sampled haplotypes are used to determine the most likely arrangement of alleles on each chromosome. Depending on the phasing algorithm, constraining the search space does not necessarily guarantee that the reads will be incorporated into the HMM. For instance, in fastPHASE, the HMM state space is constructed independently of the Gibbs sampling step. ShapeIT is somewhat unique in that the results of the Gibbs sampling are directly fed back into the construction of the HMM. This was an important motivation for the selection of ShapeIT as one example embodiment. Regardless of whether reads are incorporated into the HMM or not, the approach presented here guarantees that the phasing of a particular individual is compatible with sequencing data, and is constant in computational time (instead of linearly increasing time or polynomially increasing time) regardless of the chromosome or number of markers to phase. The main advantage of incorporating reads into the HMM is that such a step can help improve the accuracy of the phasing in other individuals in the population as well. Once read-compatible haplotypes have been sampled, they influence the computation of probabilities in the subsequent round of HMMs to favor the phasing configurations that are consistent with the read data.

In ShapeIT, the HMM is a Compact Hidden Markov Model (CHMM). The CHMM is a compact, efficient representation of the conventional haplotype HMM, in which the different haplotypes represented in the population are grouped into a common hidden state based on local similarities (e.g., haplotypes that are identical over the span of a subset of adjacent SNPs are considered to derive from the same state in that region).

In most phasing algorithms, the posterior probability is defined as the probability of the next SNP being 0 or 1 given the value at the previous SNP. This has been done historically so as to minimize the switching error, which indicates the proportion of heterozygous SNPs incorrectly phased with respect to their neighbors. ShapeIT is somewhat unique in that it considers transition probabilities between groups of N heterozygous SNPs. For example, if N=3, then given that the first 3 heterozygous SNPs have phase 0-1-1, what is the probability that the next set of 3 heterozygous SNPs will have a particular phase, such as 1-0-1 or 1-0-0. The number N of SNPs in each group is allowed to vary and can be set arbitrarily in both ShapeIT and seqphase. By default, N=3. Given this framework then, the sequencing reads are used to exclude possible transitions between one triplet of SNPs and the next. For example, in embodiments in which the HMM is updated, the posterior probability of such incompatible sequences of heterozygous SNPs is set to 0.

In an example embodiment, the newly developed ShapeIT model is modified. This modification accounts for phase-informative reads within a single individual for one or more individual subjects. The ShapeIT model proceeds in two major steps: 1. segmentation; and 2. Gibbs sampling.

Figure 1C:
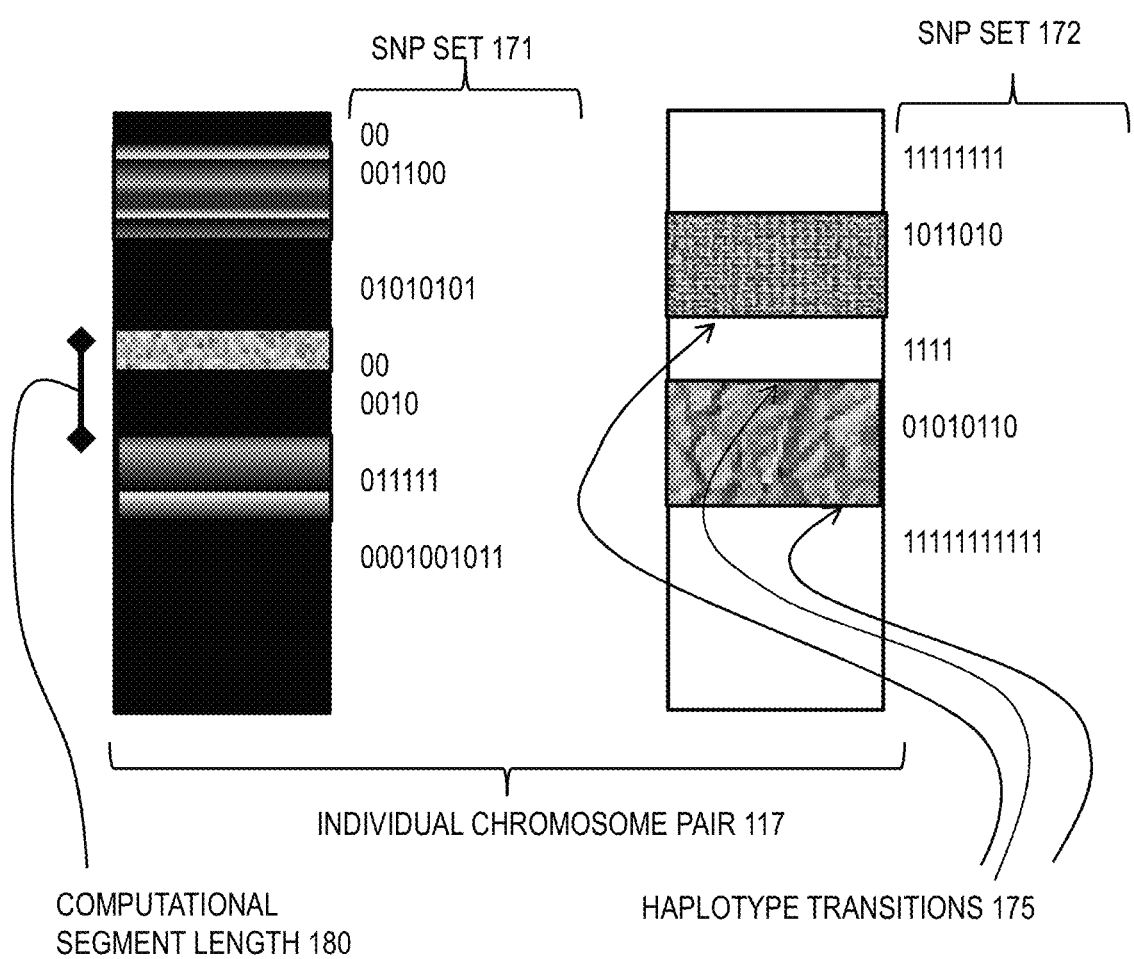
FIG. 1C is a block diagram that illustrates an example chromosome pair 117 in which each chromosome includes multiple segments of different haplotypes and a computational segment length.

In the segmentation step, the set H of all haplotypes observed in the population is collapsed into disjoint (contiguous and non-overlapping) segments of markers, across which the number of distinct haplotypes (i.e., the number of collapsed states) does not exceed a given threshold J, e.g., represented by computational segment length 180 in FIG. 1C. "Collapsed" means that, instead of looking at all H represented haplotypes over a given genomic region in the population, attention is focused solely on the set of distinct haplotypes. In other words, the universe of all haplotypes is reduced to a smaller but equally informative state space of J unique haplotypes. J is the limit per segment. It is simply a limit on the number of distinct haplotypes observed in a given genomic region. Thus, the smaller J, the more segments are needed to tile the entire chromosome. Trivially, if J is larger than the total number of chromosomes in the population, then the entire chromosome is treated as a single segment.

Figure 3A:
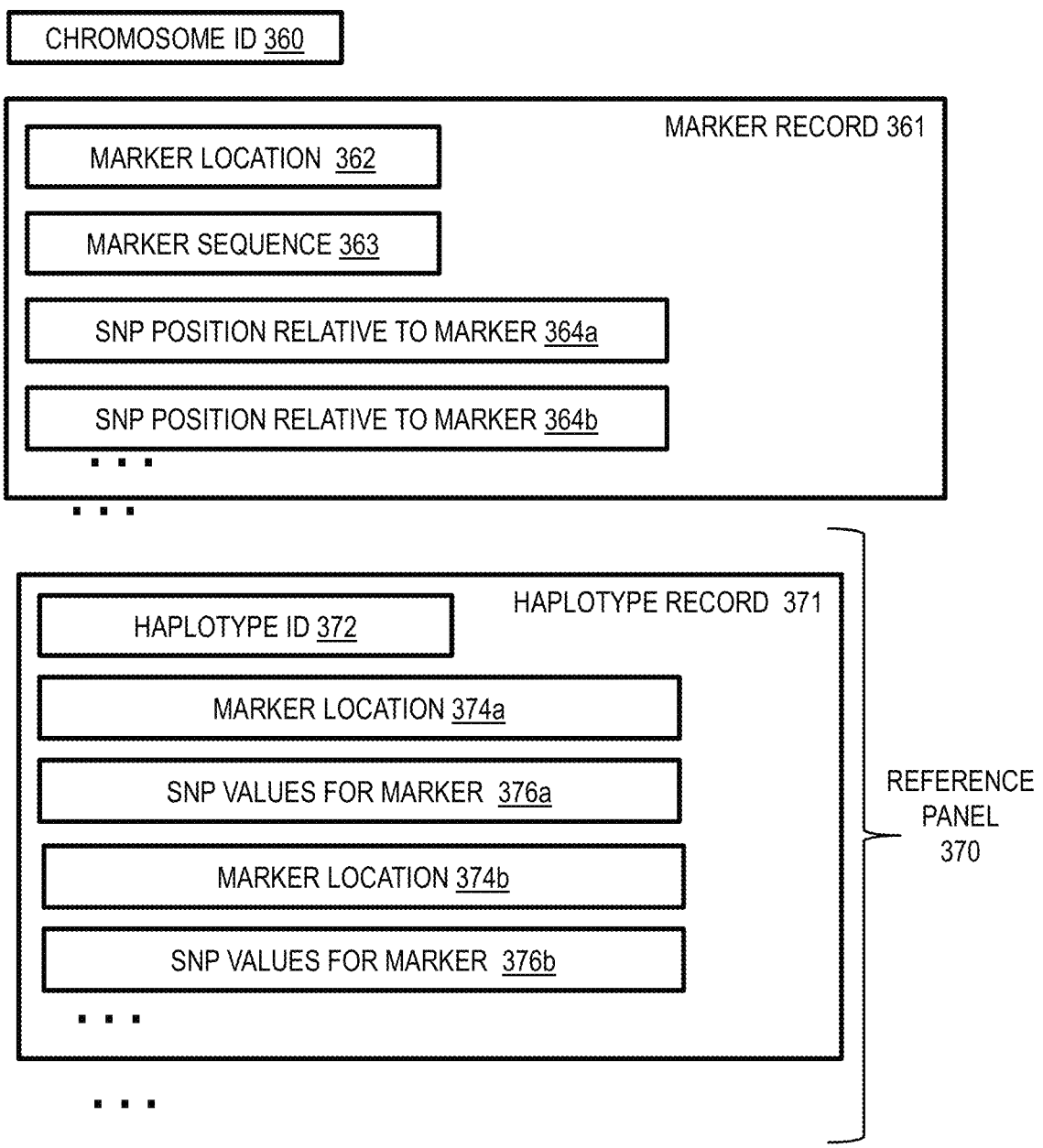
FIG. 3A is a block diagram that illustrates an example data structure for storing marker and SNP data and haplotype reference panel, according to an embodiment.

FIG. 3A is a block diagram that illustrates an example data structure for storing marker and SNP data and haplotype reference panel, according to an embodiment. Although fields and records are shown as integral blocks for purposes of illustration, in other embodiments the information indicated is provided in one or more different fields or is combined or omitted or changed in some combination of ways. This data structure represents the full haplotype information H. The chromosome of interest is identified in field 360. Chromosomes are usually referred to by number or letter, regardless of the species. Sex chromosomes are often described by a letter (e.g. chromosome X, Y etc), whereas autosomal (non-sex) chromosomes are identified by a number.

The chromosome ID field is followed by information about all the markers on the chromosome, each marker described in a separate marker record 361, with other markers described in other records 361 indicated by ellipsis. Each marker record 361 includes a marker location field 362 that holds data that indicates where on the chromosome the marker is located, whether by first base number or last base number or some other way for specifying a location for the marker position. The unique sequence that defines the marker is included in field 363. The positions of one or more SNPs associated with each marker are given in fields 354a, 364b, among others, if any, represented by ellipsis inside record 361.

A reference panel portion 370 of the data structure lists the known values of the SNPs in some consensus haplotypes for the population. Information about all the haplotypes for the chromosome is also included. Each haplotype is described in a separate haplotype record 371, with other haplotypes for the population described in other records 371 indicated by ellipsis. Each haplotype record 371 includes a haplotype identifier (ID) field 372 that holds data that indicates the haplotype. Any haplotype naming convention may be used in various embodiments. For each marker on the chromosome, indicated by marker location fields 374a and 374b, among others indicated by ellipsis inside record 371, the values of the SNPs associated with the marker are indicated in field 376a, and field 376b, respectively, among others indicated by ellipsis inside record 371.

Figure 3B:
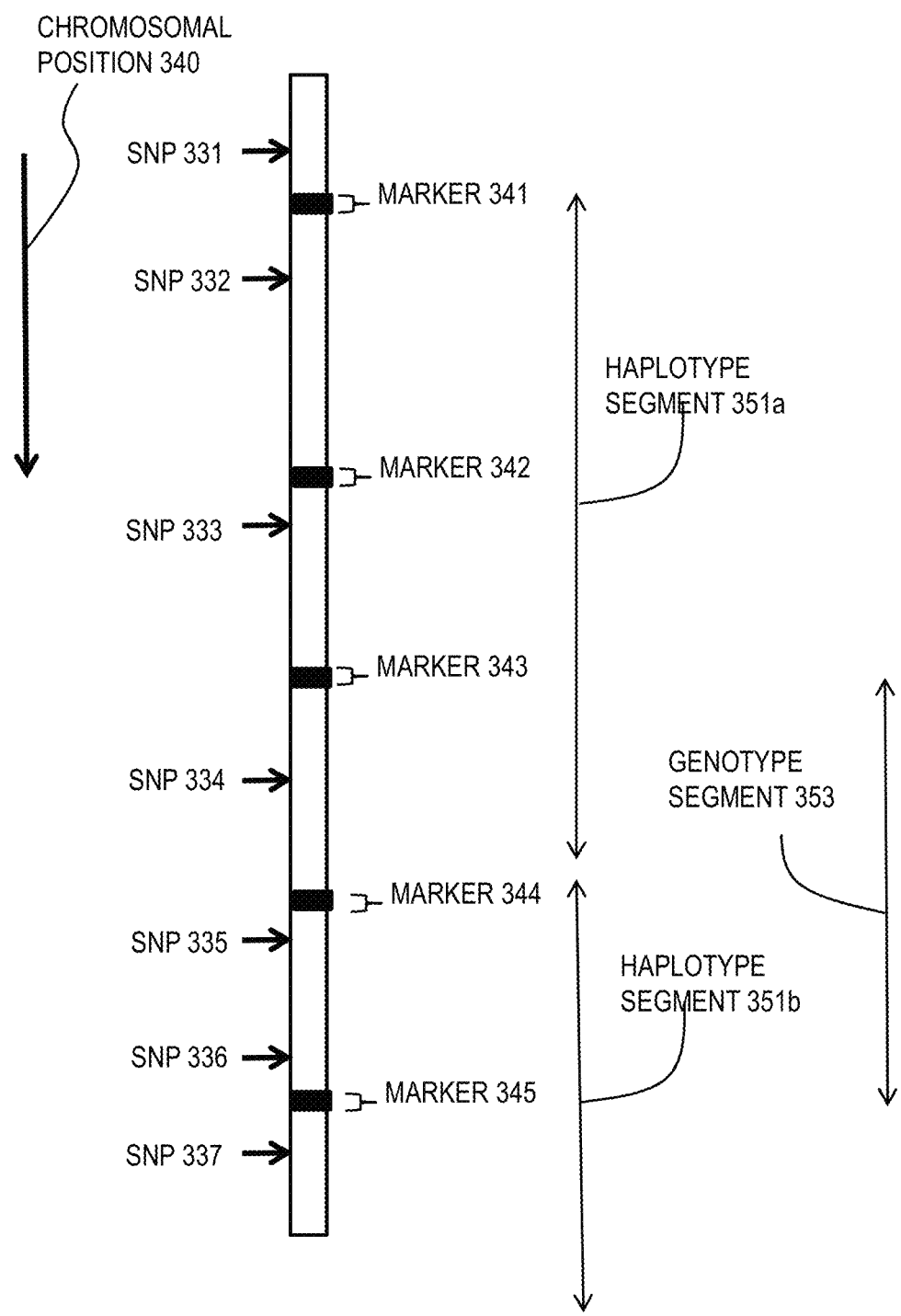
FIG. 3B is a block diagram that illustrates example haplotype segments of markers and SNPs along a chromosome, according to an embodiment.

FIG. 3B is a block diagram that illustrates example haplotype segments 351a, 351b of markers 341, 342, 343, 344, 345 and SNPs 331, 332, 333, 334, 335, 336, 337 along a chromosome indicated by chromosomal position 340, according to an embodiment. Each segment is designated Sg and the union of these segments of collapsed states is denoted as Hg. The union represents all distinct haplotypes in the population. The union is essentially a state space from which to sample possible solutions to the phasing problem. This step constrains the complexity of the algorithm to be linear in the number J of collapsed states per segment, and hence to be independent of the total number of haplotypes in the population. This feature makes the algorithm highly tractable to large-scale datasets.

Once Hg, the set of all distinct haplotypes within each segment, is defined, the sampling process follows the Li and Stephens (2003) model (N. Li and M. Stephens, "Modeling linkage disequilibrium and identifying recombination hotspots using single-nucleotide polymorphism data," *Genetics* v165 n4, pp 2213-33, 2003) of haplotypic diversity in the population. Briefly, the model treats every chromosome as a mosaic of ancestral haplotype blocks. This discretized structure is modeled as a Hidden Markov Model (in this case, a Compact Hidden Markov Model, or CHMM), with J hidden states (the J haplotypes in the collection of segments). Transitions (or jumps) from one haplotype to the next are modeled as Poisson processes, and hence the arrivals of jump events along the chromosome are exponentially distributed. The rate parameter is actually a function of the genetic distance between two adjacent markers, as well as of the effective population size. Specifically, the probability of a transition is as given by Equation 1, $$p(z_{m+1} = k_{m+1} \mid z_m = k_m) = (1 - \rho_m) \frac{c(k_m, k_{m+1})}{c(k_m)} + \rho_m \frac{c(k_{m+1})}{K} \quad (1)$$

where $\rho_m$ is the probability of recombination between markers m and m+1 as defined in Li and Stephens 2003, K is the total number of haplotypes in H, km represents one of J possible states in a given segment. In other words, km is one of J distinct haplotypes in the population. The variable c(km) represents the number of times this particular haplotype has been observed in the entire population. If the haplotype is seen in a single chromosome, c(km)=1. If the haplotype is seen in every single chromosome of the population, c(km)=K. The variable zm is the hidden haplotype state {member of set 1 to J] in the CHMM at marker m. The term c(km, km+1) is the number of times a transition from haplotype km to haplotype km+1 is observed in the population In the Gibbs sampling step, individual haplotypes are sampled from the CHMM. Specifically, a forward-backward-expectation algorithm is executed to compute the posterior probability that a given genotype can be explained by the pairing of any two sampled (or simulated) haplotypes $h_1$ and $h_2$ (henceforth referred to as the diplotype $(h_1, h_2)$). This is a standard forward backward algorithm, as applied in the HMM literature. It is a dynamic programming based method that estimates the posterior state probabilities in linear time, by exploiting favorable properties of the underlying Markov Chain. The "expectation" step simply refers to the Gibbs sampling step, which is applied based on the posterior probabilities estimated by the forward backward algorithm. The output of the forward-backward algorithm is a set of $2^J$ probabilities, one for each combination of haplotypes with replacement. For any given individual, the sampled haplotypes are constrained by the genotypes of the individual.

While the space S of all possible haplotypes compatible with these genotypes is intractably large for even small datasets, this computational limitation can also be circumvented by segmentation. In ShapeIT, the vector of genotypes for the individual is broken down into consecutive segments, such as genotype segment 353 in FIG. 3B each segment having a fixed number B of consecutive ambiguous markers (either heterozygous or missing in that particular individual, where B=3 in the seminal paper), each with eight possible haplotypes. Heterozygous markers as used herein refer to markers for associated SNPs that are heterozygous in a given individual (and hence for which phasing is ambiguous). For example, if SNPs 334, 335 and 336 in FIG. 3B are heterozygous, then a genotype segment 353 is broken out of the markers 343 and 344. The expectation is that such short segments 353 can be completely explained by just two haplotypes. From one triplet to the next, there are $2^8$=64 transitions that are of interest. The probabilities of each of these transitions are estimated by simulation, via the Gibbs sampling scheme.

The aim of the Gibbs sampler is thus to estimate the most likely diplotype transitions between each pair of consecutive genotype segments, with one haplotype pair associated with each genotype segment. Each segment contains B heterozygous SNPs. For example, when B=3, then each segment contains $2^3$=8 possible haplotypes, for each of the possible configurations of alleles. The next segment also has 8 possible haplotypes. One is thus looking at all 64 possible transitions between any two adjacent segments. Of course, the power of the method presented here rests on the fact that the sequencing reads can eliminate many of these transitions, thus significantly increasing the accuracy of the resulting phasing. This goal is achieved by consecutively sampling adjacent segments in $S_g$ based on the forward and backward probabilities derived from the CHMM, e.g., the probability that a haplotype transition has occurred between segments. If the likelihood of a haplotype transition is small between segments 351a and 351b, then the most probable haplotype pair in genotype segment 353 is probably the correct haplotype pair for segment 353. To summarize, the forward backward algorithm generates a set of $2^J$ posterior probabilities for each pair of segments within Hg. However, these probabilities are not used directly for phasing: rather, they are then used to sample a combination of triplets of SNPs by Gibbs sampling. Ultimately, the transition probabilities between each set of triplets and the next are used to obtain a best guess for the phasing.

Figure 2:
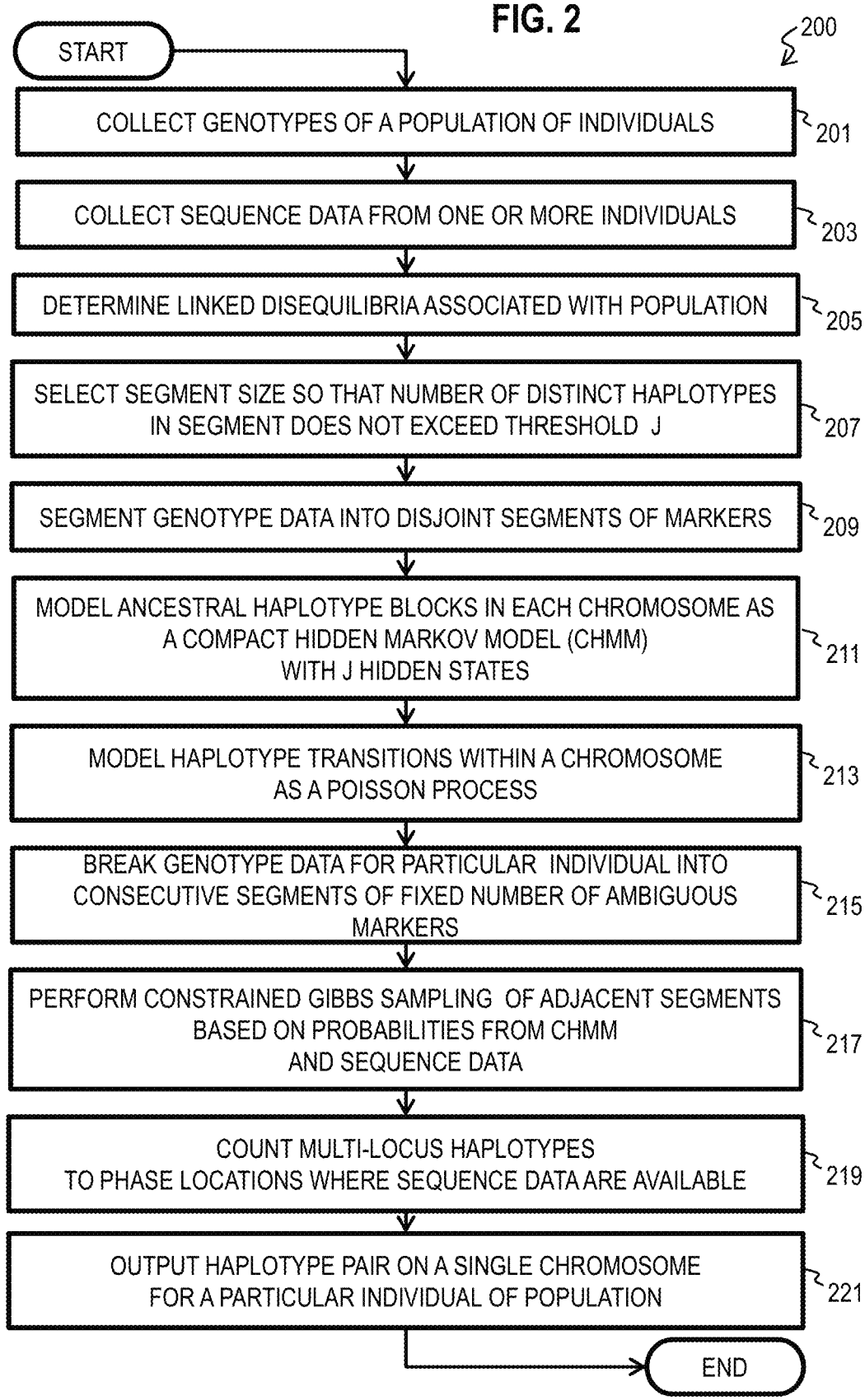
FIG. 2 is a flow diagram that illustrates an example method for determining haplotype by population genotype and sequence data, according to an embodiment.

According to various embodiments, the probabilities of the HMM are adjusted to remove probabilities for transitions that are inconsistent with the sequencing data. In general, FIG. 2 is a flow diagram that illustrates an example method for determining haplotype by population and sequence data, according to an embodiment. Although steps are depicted in FIG. 2 as integral steps in a particular order for purposes of illustration, in other embodiments, one or more steps, or portions thereof, are performed in a different order, or overlapping in time, in series or in parallel, or are omitted, or one or more additional steps are added, or the method is changed in some combination of ways. Steps 201, 205, 207, 209, 211, 213, 215 are as described above for the standard model.

Step 203 is added in the illustrated embodiment to collect sequencing data from one or more individuals from the population being phased, e.g., by obtaining ultra-high throughput sequencing data. For example, paired end reads are obtained during step 203. The inclusion of paired end read data can provide local phasing information between select pairs of heterozygous sites. These sites may be spanned by a single read, or by two separate reads linked by an unsequenced insert. FIG. 3C is a table that illustrates example values for SNPs physically linked by sequence data, according to an embodiment. For comparison the table is arranged as in FIG. 1D. FIG. 3C shows that SNPs at positions 6, 7, 8, 12 and 13 were found to have the values of 1,0,0,1,0, respectively, on the same chromosome. With the genotype data in FIG. 1D indicating that positions 7 and 8 are heterozygous, the values 00 at these positions in the sequence data rules out haplotypes with 1, 0 or 0,1 at these positions. The other haplotype in the individual must have values 11 at these positions. The sampled haplotypes from the Gibbs sampling of the most probable haplotype pair in a segment including these positions is constrained by this sequence information—thus the term "constrained Gibbs sampling."

Let $\Omega$ denote the set of all pairs of genotypes phased using the sequencing data, and let $\Omega'$ denote the subset of those phasings that are incompatible with the haplotypes derived from a standard algorithm such as fastPHASE, Beagle or ShapeIT. Assuming for now that there are no errors in the sequencing data, the pairs of heterozygous sites in $\Omega'$ represent actual phasing errors in the algorithm. In subsequent steps, the inferences of the algorithm are corrected wherever sequence read information is available. Correction is achieved through a two-step modification of the original algorithm, represented by step 217 and step 219. In step 217, a constrained version of the Gibbs sampler is implemented to sample combinations of heterozygous sites that are consistent both with the sequence data and with haplotypes resolved from the population, as described in more detail below. In step 219; multi-locus haplotypes (haplotypes carrying multiple ambiguous markers) are counted (that is, the number of times that a given haplotype appears throughout the course of the Gibbs sampling process is counted) instead of counting pairs of segments, thus phasing those sites where sequence data are available. The multi-locus haplotypes that are being counted here are constructed in such a way as to be compatible with the read data. This is a direct consequence of the constrained Gibbs sampling method described here.

In step 221, the haplotypes for the population are output and the most likely set of alleles on each chromosome of the pair of chromosomes for an individual is output by the process. In general, most downstream applications for phasing are interested in the most likely combination of haplotypes that makes up an individual's genotypes. Thus, the algorithm outputs this most likely solution, which corresponds to a most likely assortment of alleles along the chromosome for the individual. That specific set of alleles is the individual's haplotype, made up of one or more haplotypes for the population which are the J states of Hg.

In some embodiments, step 203 includes clustering of the read data. For computational reasons, much of the algorithm relies on the principle that every SNP is linked to no more than one other SNP in each of both directions along the chromosome (maximum of two links). Naturally, the read data generated by conventional sequencing platforms do not generally conform to this idealized distribution. To adapt the raw read relationships to the desired input for the algorithm, a pre-processing step is executed to "daisy chain" clusters of SNPs that are linked together by complex relationships in the read data. As an example, suppose that three SNPs labeled A, B, C are distributed along the chromosome, in this order. Suppose that, according to the read data, the following phase relationships are indicated:

A-B; allele relationship: 0-1
A-C; allele relationship: 0-0

This arrangement does not conform to the algorithm input, since SNP A is linked to two SNPs downstream along the chromosome. After the pre-processing step, two artificial links are created:

A-B; allele relationship: 0-1
B-C; allele relationship: 1-0

That is, the allelic phase between markers B and C has been inferred based on what is known of the phase between A and B, and between A and C. Formally, the daisy-chaining algorithm proceeds by forming clusters of SNPs based on the read data. SNPs that can somehow all be physically linked to each other by the reads are stored into separate, self-containing groups of markers. Once these groups have been formed, the links are re-arranged so that each SNP is joined to the SNP immediately preceding it and the SNP immediately following it based on the chromosome coordinate.

In some embodiments, step 203 includes special treatment of singletons, e.g., SNPs that occur only once, or extremely rarely, in the population. Singletons are variants that are observed on a single haplotype in the sample. Since they are not observed in any other individual in the sample, they are by definition impossible to phase using genotype data alone. However, singletons that happen to be linked to a neighboring heterozygous site by one or more sequencing reads can be phased deterministically, by using the phase of the linked site as a proxy to infer the phase of the singleton. This feature of singletons is a key driver of the advantage of current embodiments with respect to other state-of-the-art phasing algorithms. The incorporation of read data enables various embodiments to substantially outperform the other methods when trying to phase rare variants, for which the statistical power for population-based haplotyping is limited.

Singletons are the most common category of variants found in the sample, so it is critical to properly phase them. The treatment of singletons in the context of various embodiments is not straightforward. On the one hand, simply including those singletons for which phase-informative read data are available ensures that they are properly phased with respect to their linked SNPs. On the other hand, the inclusion of singletons in the reference panel (i.e. the full set of haplotypes represented in the population) can come at the cost of breaking up or skewing linkage disequilibrium patterns between neighboring SNPs (especially if they are also relatively rare variants). Also, it is fairly common for a singleton to act as a physical bridge between SNPs that are otherwise too far apart to be linked by sequencing read data; in such scenarios, simply ignoring the singletons could lead to the loss of phasing information between those other SNPs, which in turn would result in phasings that are not entirely consistent with the read data.

To address these different issues, the following steps were implemented within step 203 prior to the start of the population phasing. For singletons with a single physical link to another SNP, the singleton and the phasing inferred from the read data are recorded in a target panel structured like the reference panel of FIG. 3A, and the singleton is removed from the target panel. In some embodiments, the information is stored in a map. For example, suppose that SNP1 at position 1234 is a singleton, linked by a read to SNP2 at position 5678. In some embodiments, this information is stored as follows: 5678 maps to singleton 1234 if the phase is 1-1 or 0-0. Otherwise, 5678 maps to singleton −1234. In other words, the position of the singleton is recorded as the absolute value of the mapping, and the phasing is recorded by the sign of the mapping. The target panel holds the sequence of SNP values on one chromosome and is used to match to a haplotype in the reference panel, at least one or more segments at a time. At the end of the phasing algorithm, the singleton is deterministically added back into the target panel based on the phase configuration of the target SNP.

Singletons with two physical links are useful for daisy-chaining, because, if a singleton is linked to flanking target SNPs by the read data, thus acting as a bridge between those target SNPs, the algorithm accounts for the frequency of the two target SNPs. If both target SNPs are non-singletons, then the singleton is removed from the target panel, and a physical link is recorded between the two flanking SNPs, thus guaranteeing that their phasing will be consistent with the read data. At the end of the algorithm, the singleton is added back into the target panel, in relation to the target SNPs. If one or more of the target SNPs are singletons, then the read data is followed in each direction along the chromosome to determine each of those is in turn linked to a non-singleton SNP. If so, the procedure outlined above is followed to ensure that the algorithm records a link between the non-rare variants. Otherwise, the relationship between the chained singletons is recorded, and the rare variants are collectively excluded from the phasing target panel until the very end.

In some embodiments, step 217 to perform the constrained Gibbs sampling includes causing the Gibbs sampler to be constrained based on two factors. The first factor includes haplotypes within a segment that are inconsistent with the read data. For SNPs that are relatively close to one another and for which read data are available, it is possible to immediately exclude haplotypes within a segment, thus constraining the set of possible transitions from the previous segment.

Figure 3D:
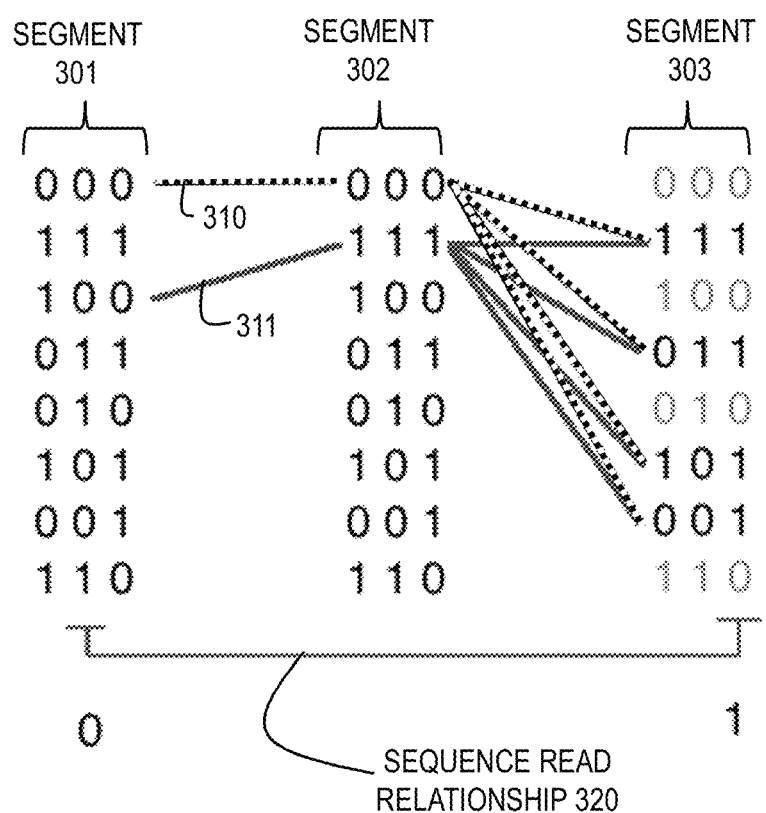
FIG. 3D is a block diagram that illustrates an example constrained Gibbs sampling algorithm, according to an embodiment.

The second factor includes haplotypes inconsistent with read data pertaining to a segment that has already been sampled. Every time a diplotype is sampled within a segment, the set of compatible diplotypes at subsequent segments is constrained by the read information at that segment. This factor is illustrated in FIG. 3D. FIG. 3D is a block diagram that illustrates a constrained Gibbs sampling algorithm, according to an embodiment. In this illustrated embodiment, the graph Sg is comprised of 3 segments, designated segment 301, segment 302, segment 303, respectively, of three SNPs each, represented by three values selected from {0, 1}. The graph shows every possible arrangement of 3 SNPs at each of the three segments. The lines 310 and 311 represent possible samplings over Sg. Suppose that a sequencing read relationship requires a certain phasing configuration between SNP2 from segment 1, and SNP3 from segment 3, namely that a value of 0 at SNP2 from segment 1 requires a value of 1 at SNP3 from segment 3, as indicated by the relationship 320 signified by a line connecting the two SNPs from different segments. Then the space of compatible haplotypes given the observation of 000 or 100 in segment 1 (lines 310 and 311, respectively) becomes constrained to have a value 1 in the third SNP position of the third segment 303 (invalid haplotypes in segment 3 shown in gray).

In step 219, different counting is done than in the original algorithm. The original algorithm carries out phasing by counting the most common pair of alleles that arise at adjacent segments in the simulation (e.g., the Gibbs sampling scheme). However, this approach is often not consistent with available sequence data. By solely focusing on adjacent pairs of segments, the more complex phasing relationships that can be gleaned from the reads would be ignored. As a result, it would be impossible to ensure that the final phasing would be faithful to the sequence data.

Instead, in some embodiments of step 219, entire haplotypes are counted wherever sequence data are available. To this end, the chromosome under consideration is subdivided into discrete adjacent blocks covered by informative reads. In this case, haplotypes are broken down into blocks based on the patterns of read data. In other words, every block is a segment of the haplotypes. Starting from one end of the chromosome, a given block starts at a heterozygous site that is linked by paired end sequence reads to a downstream heterozygous site (but not to any upstream sites). The block ends when a heterozygous site is reached beyond which there are no more downstream links (e.g., no links originating inside the block terminate downstream of that site). For example, the read data illustrated in FIG. 3C would define a block that extends from a marker for SNP positions 6 through a marker for SNP position 13. Each block is then phased by selecting the multi-locus haplotype that appears most frequently in that block. Naturally, sites for which no sequence data are available are phased using the standard method.

This embodiment has been evaluated as described next. Traditionally, the benchmark of performance for any phasing algorithm is the switch error $S_{err}$ (Sheet and Stephens 2006), defined as the ratio of incorrectly phased heterozygous sites $h_{err}$ to the total number of heterozygous sites $h_{total}$, given by Equation 2.

$$S_{err} = \frac{h_{err}}{h_{total}} \quad (2)$$

To assess the performance of the algorithm, HapMap individuals genotyped at high density on the Affymetrix Axiom chip were considered. These individuals are grouped into 4 different populations: the Yoruba from Nigeria (YRI), CEPH Europeans sampled from Utah (CEU), Chinese from Beijing (CHB), and Japanese from Tokyo (JPT). Pseudo-individuals of known phase were constructed by randomly pairing full X chromosomes (excluding pseudo-autosomal region) from males in each population. These pairings yielded 14 YRI, 14 CEU, 11 CHB and 10 JPT pseudo-females (XX). Since it is desirable to compare the relative improvement in phasing afforded by the inclusion of sequence data in each of the populations, these sets of individuals were augmented with additional female X chromosomes. Specifically, the YRI and CEU sets were augmented with 29 females each, yielding two sets of 43 individuals. For the Asian populations, the JPT and CHB simulated females were combined and another 22 females randomly drawn from a pooled set of JPT and CHB individuals were included.

To assess the effect of incorporating paired end read data on overall switch error rates and correct haplotype length distributions on the Axiom data, paired end reads that would be expected from an Illumina Hi-Seq 1000 run were simulated. Specifically, reads 100 bp in length each, throughput of 200 Gb, and an average insert size of 500 bp were assumed. To simulate some of the read variability inherent to library construction, insert sizes for every read from a normal distribution centered at 500 bp and with standard deviation 100 bp were sampled. Throughout the simulation, only those reads that span at least two heterozygous sites were included.

To assess the performance of the algorithm, the method was first applied to simulation data based on densely genotyped HapMap individuals across 7,745,081 SNPs on the Affymetrix Axiom chip, simulating reads generated by high throughput sequencing. To this end, we generated three equally sized datasets representative of three continental groups: the Yoruba from Ibadan (YRI), CEPH Europeans from Utah (CEU), and Chinese from Beijing and Japanese from Tokyo (CHB+JPT). Similarly to Delaneau et al. (O. Delaneau, J. Marchini, and J. F. Zagury, "A linear complexity phasing method for thousands of genomes," *Nature Methods* v9 n2, pp 179-81, 2011) and Sheet and Stephens (P. Scheet and M. Stephens, "A fast and flexible statistical model for large-scale population genotype data: Applications to inferring missing genotypes and haplotypic phase," *American Journal of Human Genetics*, v78 n4, p629, 2006), our focus was on the X chromosome—genotyped at 156,041 SNPs—generating pseudo-females of known phase by randomly pairing the X chromosomes of the males in each group. Reads based on the average characteristics of a standard Illumina run with a 500 bp insert (see methods) were then simulated. These data enabled computation of switch errors for each population, in the presence and absence of read data (i.e. standard ShapeIT).

The results from these experiments are summarized in Table 1, where seqphase refers to an example embodiment that includes sequence reads. First, the phasing in this scenario yields error rates that are substantially lower than any reported in the literature; previous studies have generally reported error rates on the order of 5% to 6% (S. R. Browning and B. L. Browning, "Rapid and accurate haplotype phasing and missing-data inference for whole-genome association studies by use of localized haplotype clustering," *American Journal of Human Genetics* v81 n5, pp 1084-9'7, 2007). These low error rates are most likely due to the nature of the data themselves: namely, the high density of the markers afforded by high density genotyping and high throughput sequencing enables the inference of highly accurate haplotypes. This effect is likely compounded by the lower effective population size that is characteristic of sex chromosomes. Second, comparing across populations, it is clearly seen that the standard algorithm performs most poorly on the YRI, followed by the CEU and finally the Asian populations. Factoring in the simulated read data leads to roughly similar improvements in phasing across populations, on the order of 7.0% to 8.3%.

TABLE 1

Comparison of switch error rates between different phasing methods on the three HapMap populations genotyped on the Axiom chip. Improvements using seqphase displayed in parentheses.

| Population | Het markers | Beagle | FastPHASE | ShapeIT | seqphase |
|---|---|---|---|---|---|
| YRI | 113,847 | 3.90% (−55.6%) | 3.10% (−44.2%) | 2.05% (−15.2%) | 1.73% |
| CEU | 86,870 | 2.88% (−42.4%) | 2.55% (−34.9%) | 1.86% (−10.8%) | 1.66% |
| JPT + CHB | 79,391 | 2.82% (−29.1%) | 2.47% (−19.0%) | 2.25% (−11.1%) | 2.00% |

The performance of the illustrated embodiment was next compared relative to Beagle, another state of the art phasing algorithm. Previous results in the literature generally appear to suggest that Beagle and fastPHASE perform roughly similarly, with fastPHASE performing better on smaller datasets; conversely, ShapeIT has recently been shown to outperform these two algorithms for a wide range of sample sizes. Thus, the previous analyses was repeated on each of the three populations using Beagle, fastPHASE, and ShapeIT. Beagle was run using 10 iterations (the authors state that increasing this number only negligibly improves phasing) and R=25 samples, recommended by the authors for high quality phasing.

It was generally found that both ShapeIT and the illustrated embodiment, seqphase, universally outperformed the other two in all three datasets, with improvements of about 30%. These results are encouraging for two reasons. On the one hand they justify the choice of using ShapeIT as the backbone for the illustrated embodiment, since it already performed the best in the absence of sequence data. On the other hand, these observations confirm that, by incorporating sequencing information, a method has been developed that can outperform these three state-of-the-art methods in the presence of reads.

As described in the manuscript, the ShapeIT method developed by Delaneau et al. is a genotype-based phasing algorithm. The method takes in genotypes from unrelated individuals, and then uses an HMM-based graphical framework to identify patterns of linkage disequilibrium between subsets of SNPs in the genome. These estimates are refined in an iterative fashion by sequentially phasing individuals in the population based on the inferred haplotypes of all of the others in the sample. The critical difference between seqphase and ShapeIT (and by association, any other conventional genotype-based phasing algorithm) is that ShapeIT is completely agnostic to sequencing read data. ShapeIT does not take any sequencing information into account, and there is no straightforward approach to incorporate phase relationships inferred from the read data into the current implementation of this method.

The method presented by He et al. approaches the phasing problem from a different angle than the other phasing methods (fastPHASE, Beagle, ShapeIT) described previously. These algorithms are known as population-based phasing methods: they infer and subsequently exploit linkage disequilibrium patterns from the genotype calls of a population to obtain maximum likelihood guesses for haplotypes. Conversely, the method presented by He et al. addresses the problem of genome assembly in a single individual. Specifically, the approach of He et al. harnesses a large library of DNA fragments generated through shotgun sequencing to assemble the genome of the target individual, and by extension, to determine which fragments map to the maternal versus paternal chromosome in that individual. This approach is best suited for de novo genome assemblies, which usually involve the use of a wide array of sequencing libraries (with different read and fragment sizes) so as to capture both short and longer range sequence relationships in the target genome. Note, however, that unlike the other phasing methods, this method makes no use of population-level phasing relationships. Hence, the method is less amenable to phasing low- and medium-coverage datasets, such as the Thousand Genomes Project.

Unlike the method by He et al. and the other conventional population-level phasing methods described above, the seqphase embodiment is the first hybrid method to make use of both sequencing read data for molecular phasing, and population-level phasing for regions that do not have the requisite sequencing coverage to be phased deterministically.

The Haplotype Improver (HI) method described by Long et al. (2009) is closest to the illustrated embodiment seqphase in that it too attempts to improve haplotype phasing using sequencing read data. The algorithm is a post-hoc phasing method. It starts from an initial guess for haplotypes generated from genotypes only using a conventional method such as fastPHASE or Beagle. HI attempts to reconcile the generated phasing with supplied sequencing read data, using a maximum likelihood approach. To this end, the algorithm relies on likelihood estimates for the phasing at each pair of adjacent SNPs. There are three differences between HI and seqphase. First, HI is applied on an individual-per-individual basis: the improvement of phasing in one individual does not influence that of the other individuals in the sample. In contrast, seqphase incorporates the read data at every update step of the Gibbs sampler, so that each improved haplotype serves as a template for the others in the context of the CHMM framework described above. Second, the fact that HI is applied after the population-level phasing (instead of being directly interwoven into the statistical haplotyping algorithm, as is the case in seqphase) limits the quality of the improvements offered by HI. The HI authors generally reported an improvement in switch error on the order of 2% to 3% with respect to fastPHASE, which contrasts sharply with our reported improvements of 5% to 15%. Furthermore, the complexity of HI is linear in the number of reads, whereas seqphase is constant in the number of reads (the addition of reads simply constrains the search space of compatible haplotypes, and hence does not add significantly to computational time).

In another example embodiment, sequencing data was combined with the Complete Genomics (CG) data. Complete Genomics (CG) has released a panel of 60 genomes, taken from several different populations. The CG platform effectively generates paired end data using very short ends (35 bp each) and relatively short inserts (on the order of 300-500 bp). To assess the performance of an embodiment on empirical sequencing data, a trio of YRI individuals included in the reference panel, originally sampled as part of the HapMap project were considered. With the exception of sites that are heterozygous in the child and in both parents (labeled in HapMap as NA19238 and NA19239 for the mother and father, respectively), all genotypes in the trio can be phased without error, up to single generation recombination events that have occurred in that generation. In this embodiment, focus was directed on chromosome 22 for computational ease. As a first pass for this analysis, singletons (alleles that appear only once in the entire reference panel) were excluded. By default, these alleles cannot be phased using statistical methods, since no haplotyping information can be derived from other individuals in the population, all of which are homozygous for the major allele.

An important consideration in this embodiment lies in the construction of the phasing reference panel. Ideally, for a non-admixed population, one would use a large number of individuals drawn solely from that population (in this case, a large YRI population). However, the CG panel of 60 genomes only contains 9 unrelated YRI individuals; thus, the homogeneity in the reference population would come at the expense of statistical power. To determine a more advantageous reference panel, three reference panels were constructed: the set of 9 YRI individuals only, the set of 17 African individuals (comprised of the YRI, Luhya (LWK) and Maasai (MKK) individuals sampled from the HapMap 3 project), and finally the full set of Complete Genomics sequences. Related individuals (such as those in the CEU extended pedigree) were excluded from all phasing panels.

TABLE 2

Relative performance of Beagle, fastPHASE, ShapeIT and seqphase on the CG panel using three possible phasing reference panels.

| Reference | Size | Beagle | fastPHASE | ShapeIT | seqphase |
|---|---|---|---|---|---|
| YRI | 9 | 33.2% | 15.4% | 8.82% | 7.68% |
| African | 17 | 22.6% | 9.94% | 5.47% | 5.06% |
| Full panel | 48 | 9.96% | 7.80% | 3.68% | 3.56% |

A comparison of the performance of the example embodiment (seqphase) against ShapeIT, fastPHASE and Beagle is shown in Table 2. From Table 2, it can be seen that using the full reference panel of 48 unrelated individuals yields more accurate phasing than focusing on more homogeneous subpopulations for a reference panel. This result was found to hold for all tested algorithms. In the absence of read data, it was found that ShapeIT outperformed both Beagle and fastPHASE. In particular, Beagle performed the worst of all methods, though the overall gap in performance narrowed considerably with the inclusion of more samples: on average, ShapeIT yielded a 63.1% improvement over Beagle in the full set of individuals, versus a 73.4% improvement on the YRI-only dataset. With the inclusion of paired-end read data, seqphase yielded significant improvements in accuracy over ShapeIT, though these were more pronounced in the smaller panels. Thus, a 12.9% reduction in switch error rate was observed using the YRI alone as a reference panel, versus a smaller 3.9% reduction in the error rate observed on the full panel. This modest reduction in the number of haplotyping errors is likely a reflection of the low phasing information content of the CG reads.

Figure 4:
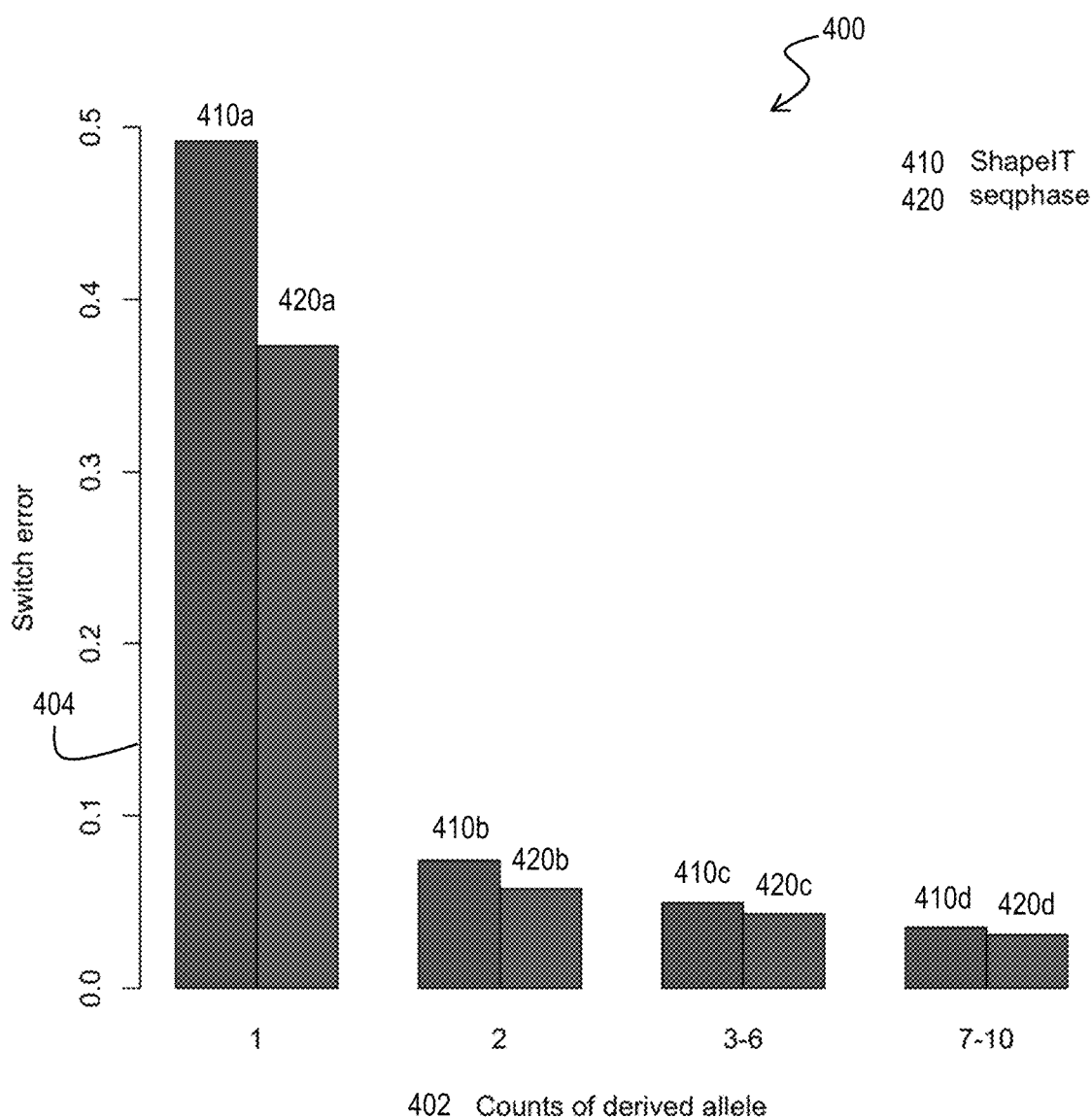
FIG. 4 is a graph that illustrates example differences in switch error versus the observed number of derived alleles in a Complete Genomics data set, both in the presence and absence of read data, according to an embodiment.

While the previous results provide an indication of the relative performance of each of the phasing algorithms on the CG panel, they do not offer much insight into the effect of allele frequencies on the quality of the haplotype reconstruction. In practice, rarer variants are expected to be phased more poorly using the conventional statistical methods, as the reference panel would contain less LD information for those sites. To better characterize the performance of these algorithms around variants with low counts in the reference panel, the number of observed switch errors was stratified based on the relative frequencies of the sites at which they were found to occur. These results are shown in FIG. 4 for seqphase and ShapeIT, FIG. 4 is a graph that illustrates example differences in switch error versus the observed number of derived alleles in a complete genomics data set, both in the presence and absence of read data, according to an embodiment. In particular, FIG. 4 depicts switch error rate in the CG panel versus the observed number of derived alleles in the full reference panel of 48 unrelated individuals both in the presence (seqphase) and absence (ShapeIT) of read data. The horizontal axis 402 indicates the count of occurrences of an allele in the population. To reduce the effect of disparities in the number of sites included in each category (e.g singletons occurring more frequently than tripletons), sites with 3-6, and 7-10 observed derived alleles were grouped. The vertical axis 404 indicates the switch error. The ShapeIT results 410 include larger errors 410a, 410b, 410c, and 410d at the various allele counts, compared to the seqphase results 420 that include smaller errors 420a, 420b, 420c, and 420d, respectively.

Two observations can be made from FIG. 4. First, clearly seen is an inverse relationship between site frequency and switch error rate—with singletons exhibiting an error rate close to 50% in the absence of sequencing read data, as expected. Second, it is seen that the incorporation of read data (seqphase) yielded the largest improvements for those variants observed least frequently in the reference panel (e.g., the largest improvement is 420a over 410a).

In another embodiment, rare variants were included in the reference panel. The comparisons presented in the previous section were performed in the absence of singletons, whose switch errors using any genotype-based method are on the order of 50%. Yet discarding these singletons altogether is rather limiting, because they can provide deep insight into the patterns of haplotypic diversity of the population under study. This information in turn could be used to substantially improve the accuracy and the resolution of downstream analyses such as local ancestry deconvolution and demographic inferences. In practice, the sequencing data can occasionally circumvent these limitations, by providing a means of recovering some of the variants that occur at very low frequencies in the reference panel. Specifically, an illustrated embodiment can phase some of those variants if they happen to be linked to another heterozygous site by paired end reads. Thus, one could consider augmenting the previous dataset with markers harboring rare variants that satisfy this condition.

To assess the feasibility of this approach, and to determine the number of potential singletons variants that can be recovered by our method, an example embodiment includes scanning the CG raw read database once more, this time retaining rare variants with at least one physical link to another heterozygous site after filtering for sequencing error. It is found that 565 (29.8%) of the 1897 singletons in NA19238 and 525 (32.2%) of the 1626 in NA19239 had a physical link to another variant site. This additional set of 1090 markers was added to the singleton-free dataset to form a new marker set, and the above experiment was repeated using the four different algorithms. The results are listed in Table 3.

TABLE 3

Phasing accuracy of Beagle, fastPHASE, ShapeIT and seqphase both in the absence of singletons, and in the presence of phase-informed (read-linked) singletons.

|  | No singletons | Read-linked singletons |
|---|---|---|
| Beagle | 9.96% | 11.80% |
| fastPHASE | 7.80% | 9.55% |

TABLE 3-continued

Phasing accuracy of Beagle, fastPHASE, ShapeIT and seqphase both in the absence of singletons, and in the presence of phase-informed (read-linked) singletons.

|  | No singletons | Read-linked singletons |
|---|---|---|
| ShapeIT | 3.68% | 5.59% |
| seqphase | 3.56% | 3.79% |

It was found that fastPHASE and Beagle yielded mean error rates of 9.54% and 11.8%, respectively, on this new marker set, corresponding to average increases of 22.6% and 18.6% for the two methods respectively. The ShapeIT algorithm recorded a 51.9% increase in the observed switch error rate. Conversely, seqphase yielded an average 3.79% switch error (a 6.5% increase). This modest increase is likely due to the incorporation of reads linking singletons to other rare variants that are also difficult to phase. Thus, the example embodiment enabled the incorporation of about a third of all singletons in each individual at a minimal cost to the overall phasing accuracy. The impact of this approach on overall phasing is anticipated to be lower in a larger and more homogeneous population.

Figure 5:
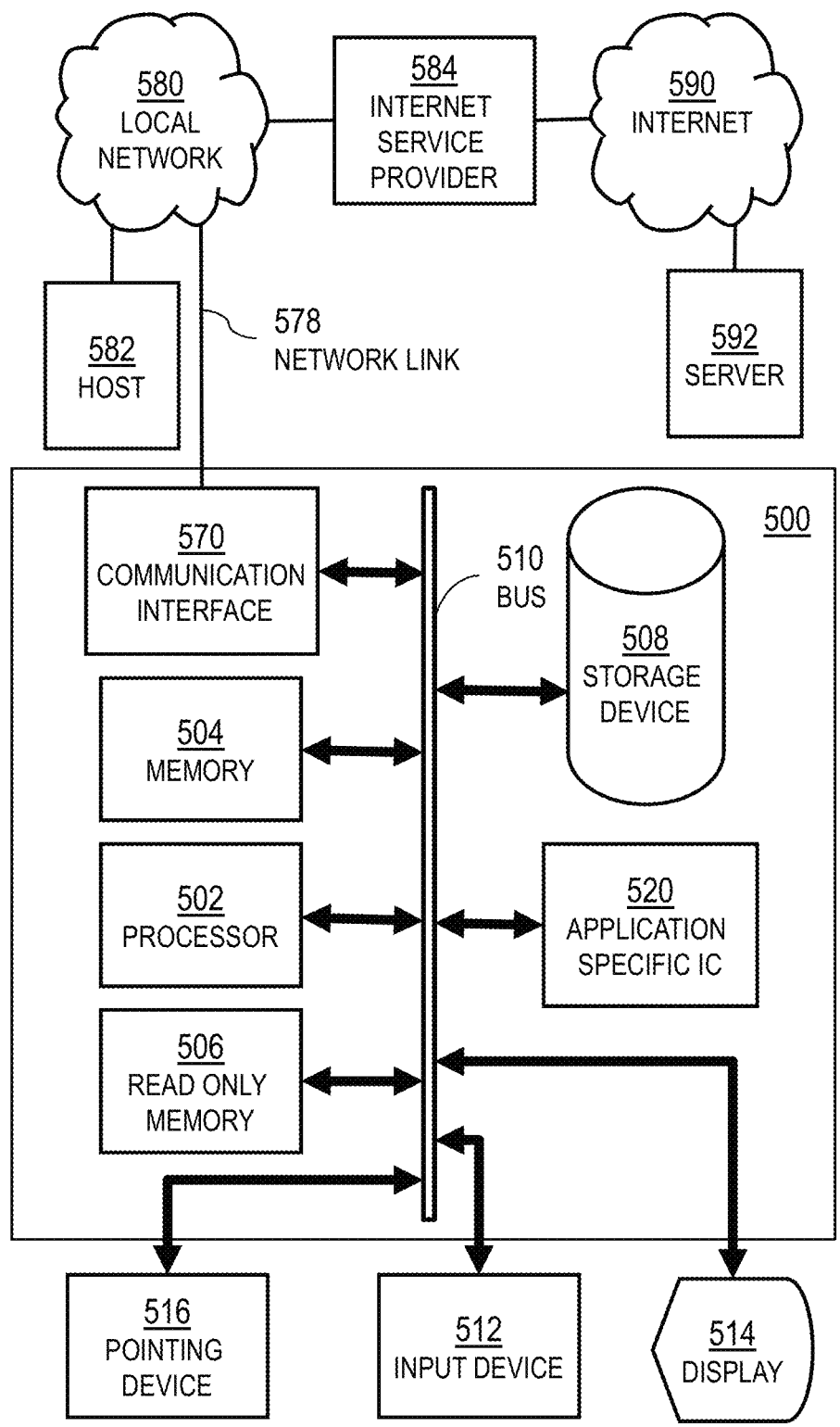
FIG. 5 is a block diagram that illustrates a computer system upon which an embodiment of the invention may be implemented.

FIG. 5 is a block diagram that illustrates a computer system 500 upon which an embodiment of the invention may be implemented. Computer system 500 includes a communication mechanism such as a bus 510 for passing information between other internal and external components of the computer system 500. Information is represented as physical signals of a measurable phenomenon, typically electric voltages, but including, in other embodiments, such phenomena as magnetic, electromagnetic, pressure, chemical, molecular atomic and quantum interactions. For example, north and south magnetic fields, or a zero and non-zero electric voltage, represent two states (0, 1) of a binary digit (bit). Other phenomena can represent digits of a higher base. A superposition of multiple simultaneous quantum states before measurement represents a quantum bit (qubit). A sequence of one or more digits constitutes digital data that is used to represent a number or code for a character. In some embodiments, information called analog data is represented by a near continuum of measurable values within a particular range. Computer system 500, or a portion thereof, constitutes a means for performing one or more steps of one or more methods described herein.

A sequence of binary digits constitutes digital data that is used to represent a number or code for a character. A bus 510 includes many parallel conductors of information so that information is transferred quickly among devices coupled to the bus 510. One or more processors 502 for processing information are coupled with the bus 510. A processor 502 performs a set of operations on information. The set of operations include bringing information in from the bus 510 and placing information on the bus 510. The set of operations also typically include comparing two or more units of information, shifting positions of units of information, and combining two or more units of information, such as by addition or multiplication. A sequence of operations to be executed by the processor 502 constitutes computer instructions.

Computer system 500 also includes a memory 504 coupled to bus 510. The memory 504, such as a random access memory (RAM) or other dynamic storage device, stores information including computer instructions. Dynamic memory allows information stored therein to be changed by the computer system 500. RAM allows a unit of information stored at a location called a memory address to be stored and retrieved independently of information at neighboring addresses. The memory 504 is also used by the processor 502 to store temporary values during execution of computer instructions. The computer system 500 also includes a read only memory (ROM) 506 or other static storage device coupled to the bus 510 for storing static information, including instructions, that is not changed by the computer system 500. Also coupled to bus 510 is a non-volatile (persistent) storage device 508, such as a magnetic disk or optical disk, for storing information, including instructions, that persists even when the computer system 500 is turned off or otherwise loses power.

Information, including instructions, is provided to the bus 510 for use by the processor from an external input device 512, such as a keyboard containing alphanumeric keys operated by a human user, or a sensor. A sensor detects conditions in its vicinity and transforms those detections into signals compatible with the signals used to represent information in computer system 500. Other external devices coupled to bus 510, used primarily for interacting with humans, include a display device 514, such as a cathode ray tube (CRT) or a liquid crystal display (LCD), for presenting images, and a pointing device 516, such as a mouse or a trackball or cursor direction keys, for controlling a position of a small cursor image presented on the display 514 and issuing commands associated with graphical elements presented on the display 514.

In the illustrated embodiment, special purpose hardware, such as an application specific integrated circuit (IC) 520, is coupled to bus 510. The special purpose hardware is configured to perform operations not performed by processor 502 quickly enough for special purposes. Examples of application specific ICs include graphics accelerator cards for generating images for display 514, cryptographic boards for encrypting and decrypting messages sent over a network, speech recognition, and interfaces to special external devices, such as robotic arms and medical scanning equipment that repeatedly perform some complex sequence of operations that are more efficiently implemented in hardware.

Computer system 500 also includes one or more instances of a communications interface 570 coupled to bus 510. Communication interface 570 provides a two-way communication coupling to a variety of external devices that operate with their own processors, such as printers, scanners and external disks. In general the coupling is with a network link 578 that is connected to a local network 580 to which a variety of external devices with their own processors are connected. For example, communication interface 570 may be a parallel port or a serial port or a universal serial bus (USB) port on a personal computer. In some embodiments, communications interface 570 is an integrated services digital network (ISDN) card or a digital subscriber line (DSL) card or a telephone modem that provides an information communication connection to a corresponding type of telephone line. In some embodiments, a communication interface 570 is a cable modem that converts signals on bus 510 into signals for a communication connection over a coaxial cable or into optical signals for a communication connection over a fiber optic cable. As another example, communications interface 570 may be a local area network (LAN) card to provide a data communication connection to a compatible LAN, such as Ethernet. Wireless links may also be implemented. Carrier waves, such as acoustic waves and electromagnetic waves, including radio, optical and infrared waves travel through space without wires or cables. Signals include man-made variations in amplitude, frequency, phase, polarization or other physical properties of carrier waves. For wireless links, the communications interface 570 sends and receives electrical, acoustic or electromagnetic signals, including infrared and optical signals, that carry information streams, such as digital data.

The term computer-readable medium is used herein to refer to any medium that participates in providing information to processor 502, including instructions for execution. Such a medium may take many forms, including, but not limited to, non-volatile media, volatile media and transmission media. Non-volatile media include, for example, optical or magnetic disks, such as storage device 508. Volatile media include, for example, dynamic memory 504. Transmission media include, for example, coaxial cables, copper wire, fiber optic cables, and waves that travel through space without wires or cables, such as acoustic waves and electromagnetic waves, including radio, optical and infrared waves. The term computer-readable storage medium is used herein to refer to any medium that participates in providing information to processor 502, except for transmission media.

Common forms of computer-readable media include, for example, a floppy disk, a flexible disk, a hard disk, a magnetic tape, or any other magnetic medium, a compact disk ROM (CD-ROM), a digital video disk (DVD) or any other optical medium, punch cards, paper tape, or any other physical medium with patterns of holes, a RAM, a programmable ROM (PROM), an erasable PROM (EPROM), a FLASH-EPROM, or any other memory chip or cartridge, a carrier wave, or any other medium from which a computer can read. The term non-transitory computer-readable storage medium is used herein to refer to any medium that participates in providing information to processor 502, except for carrier waves and other signals.

Logic encoded in one or more tangible media includes one or both of processor instructions on a computer-readable storage media and special purpose hardware, such as ASIC 520.

Network link 578 typically provides information communication through one or more networks to other devices that use or process the information. For example, network link 578 may provide a connection through local network 580 to a host computer 582 or to equipment 584 operated by an Internet Service Provider (ISP). ISP equipment 584 in turn provides data communication services through the public, world-wide packet-switching communication network of networks now commonly referred to as the Internet 590. A computer called a server 592 connected to the Internet provides a service in response to information received over the Internet. For example, server 592 provides information representing video data for presentation at display 514.

The invention is related to the use of computer system 500 for implementing the techniques described herein. According to one embodiment of the invention, those techniques are performed by computer system 500 in response to processor 502 executing one or more sequences of one or more instructions contained in memory 504. Such instructions, also called software and program code, may be read into memory 504 from another computer-readable medium such as storage device 508. Execution of the sequences of instructions contained in memory 504 causes processor 502 to perform the method steps described herein. In alternative embodiments, hardware, such as application specific integrated circuit 520, may be used in place of or in combination with software to implement the invention. Thus, embodiments of the invention are not limited to any specific combination of hardware and software.

The signals transmitted over network link 578 and other networks through communications interface 570, carry information to and from computer system 500. Computer system 500 can send and receive information, including program code, through the networks 580, 590 among others, through network link 578 and communications interface 570. In an example using the Internet 590, a server 592 transmits program code for a particular application, requested by a message sent from computer 500, through Internet 590, ISP equipment 584, local network 580 and communications interface 570. The received code may be executed by processor 502 as it is received, or may be stored in storage device 508 or other non-volatile storage for later execution, or both. In this manner, computer system 500 may obtain application program code in the form of a signal on a carrier wave.

Various forms of computer readable media may be involved in carrying one or more sequence of instructions or data or both to processor 502 for execution. For example, instructions and data may initially be carried on a magnetic disk of a remote computer such as host 582. The remote computer loads the instructions and data into its dynamic memory and sends the instructions and data over a telephone line using a modem. A modem local to the computer system 500 receives the instructions and data on a telephone line and uses an infra-red transmitter to convert the instructions and data to a signal on an infra-red a carrier wave serving as the network link 578. An infrared detector serving as communications interface 570 receives the instructions and data carried in the infrared signal and places information representing the instructions and data onto bus 510. Bus 510 carries the information to memory 504 from which processor 502 retrieves and executes the instructions using some of the data sent with the instructions. The instructions and data received in memory 504 may optionally be stored on storage device 508, either before or after execution by the processor 502.

Figure 6:
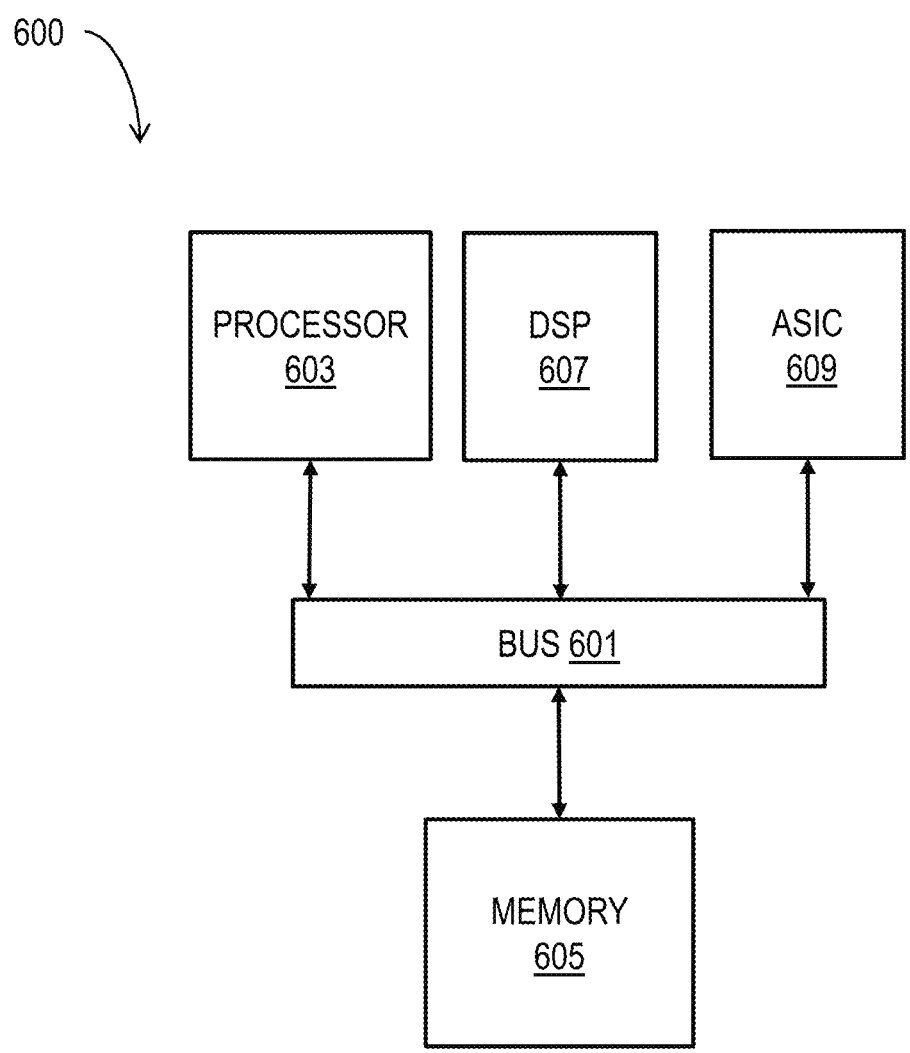
FIG. 6 illustrates a chip set upon which an embodiment of the invention may be implemented.

FIG. 6 illustrates a chip set 600 upon which an embodiment of the invention may be implemented. Chip set 600 is programmed to perform one or more steps of a method described herein and includes, for instance, the processor and memory components described with respect to FIG. 5 incorporated in one or more physical packages (e.g., chips). By way of example, a physical package includes an arrangement of one or more materials, components, and/or wires on a structural assembly (e.g., a baseboard) to provide one or more characteristics such as physical strength, conservation of size, and/or limitation of electrical interaction. It is contemplated that in certain embodiments the chip set can be implemented in a single chip. Chip set 600, or a portion thereof, constitutes a means for performing one or more steps of a method described herein.

In one embodiment, the chip set 600 includes a communication mechanism such as a bus 601 for passing information among the components of the chip set 600. A processor 603 has connectivity to the bus 601 to execute instructions and process information stored in, for example, a memory 605. The processor 603 may include one or more processing cores with each core configured to perform independently. A multi-core processor enables multiprocessing within a single physical package. Examples of a multi-core processor include two, four, eight, or greater numbers of processing cores. Alternatively or in addition, the processor 603 may include one or more microprocessors configured in tandem via the bus 601 to enable independent execution of instructions, pipelining, and multithreading. The processor 603 may also be accompanied with one or more specialized components to perform certain processing functions and tasks such as one or more digital signal processors (DSP) 607, or one or more application-specific integrated circuits (ASIC) 609. A DSP 607 typically is configured to process real-world signals (e.g., sound) in real time independently of the processor 603. Similarly, an ASIC 609 can be configured to performed specialized functions not easily performed by a general purposed processor. Other specialized components to aid in performing the inventive functions described herein include one or more field programmable gate arrays (FPGA) (not shown), one or more controllers (not shown), or one or more other special-purpose computer chips.

The processor 603 and accompanying components have connectivity to the memory 605 via the bus 601. The memory 605 includes both dynamic memory (e.g., RAM, magnetic disk, writable optical disk, etc.) and static memory (e.g., ROM, CD-ROM, etc.) for storing executable instructions that when executed perform one or more steps of a method described herein. The memory 605 also stores the data associated with or generated by the execution of one or more steps of the methods described herein.

In the foregoing specification, the invention has been described with reference to specific embodiments thereof. It will, however, be evident that various modifications and changes may be made thereto without departing from the broader spirit and scope of the invention. The specification and drawings are, accordingly, to be regarded in an illustrative rather than a restrictive sense. Throughout this specification and the claims, unless the context requires otherwise, the word "comprise" and its variations, such as "comprises" and "comprising," will be understood to imply the inclusion of a stated item, element or step or group of items, elements or steps but not the exclusion of any other item, element or step or group of items, elements or steps. Furthermore, the indefinite article "a" or "an" is meant to indicate one or more of the item, element or step modified by the article.

What is claimed is:

1. A method for measuring haplotype, the method comprising:
    providing genomic data for over 50,000 single nucleotide polymorphisms (SNPS) from a first population of individuals;
    providing linkage disequilibrium of single nucleotide polymorphisms (SNPs) in the first population of individuals;
    providing over one million reads of nucleotide bases in each of one or more individuals from a related second population of individuals who were or could have been members of the first population, based on sequencing of a sample from the one or more individuals;
    selecting segment size so that number of distinct haplotypes in segment does not exceed threshold J to collapse the number of haplotypes per segment;
    determining on a processor a haplotype included in the first population of individuals based on both the linkage disequilibrium and the plurality of reads by setting a posterior probability of a sequence of two or more SNPs determined from a statistical model for haplotype transitions per segment to a value compatible with the plurality of reads in a forward backward algorithm; and
    presenting, on a display device, data that indicates the haplotype included in the first population.

2. A method as recited in claim 1, further comprising determining the haplotype included in a chromosome of an individual based, at least in part, on the haplotype included in the first population and one or more reads of nucleotide bases for the individual.

3. A method as recited in claim 2, wherein determining the haplotype included in the chromosome of the individual further comprises determining a most likely assortment of alleles along the chromosome for the individual.

4. A method as recited in claim 1, wherein determining the plurality of reads of nucleotide bases in the one or more individuals further comprises determining the plurality of reads of nucleotide bases in the one or more individuals based on ultra-high throughput sequencing of the sample from the one or more individuals.

5. A method as recited in claim 1, wherein setting the posterior probability of the sequence of two or more SNPs determined from the statistical model further comprises setting the posterior probability from a hidden Markov Model to about zero if the sequence is not compatible with the plurality of reads.

6. A method as recited in claim 5, wherein the Markov Model output a posterior probability of a set of N heterozygous SNPs given a previous set of N heterozygous SNPs.

7. A method as recited in claim 6, wherein N is one.

8. A method as recited in claim 6, wherein N is three.

9. A method as recited in claim 1, wherein the second population is a subset of the first population.

10. A non-transitory computer-readable medium carrying one or more sequences of instructions, wherein execution of the one or more sequences of instructions by one or more processors causes an apparatus to:
    obtain genomic data for over 50,000 single nucleotide polymorphisms (SNPS) from a first population of individuals;
    provide linkage disequilibrium of single nucleotide polymorphisms (SNPs) in the first population of individuals;
    provide over one million reads of nucleotide bases in each of one or more individuals from a related second population of individuals who were or could have been members of the first population, based on sequencing of a sample from the one or more individuals;
    select segment size so that number of distinct haplotypes in segment does not exceed threshold J to collapse the number of haplotypes per segment;
    determine a haplotype included in the first population of individuals based on both the linkage disequilibrium and the plurality of reads by setting a posterior probability of a sequence of two or more SNPs determined from a statistical model for haplotype transitions per segment to a value compatible with the plurality of reads in at least one iteration of a forward backward algorithm; and
    present, on a display device, data that indicates the haplotype included in the first population.

11. A non-transitory computer-readable medium as recited in claim 10, wherein the one or more sequences of instructions executing on the one or more processors further cause the apparatus to determine the haplotype included in a chromosome of an individual based, at least in part, on the haplotype included in the first population and one or more reads of nucleotide bases for the individual.

12. A non-transitory computer-readable medium as recited in claim 11, wherein determining the haplotype included in the chromosome of the individual further comprises determining a most likely assortment of alleles along the chromosome for the individual.

13. A non-transitory computer-readable medium as recited in claim 10, wherein determining the plurality of reads of nucleotide bases in the one or more individuals further comprises determining the plurality of reads of nucleotide bases in the one or more individuals based on ultra-high throughput sequencing of the sample from the one or more individuals.

14. A non-transitory computer-readable medium as recited in claim 10, wherein setting the posterior probability of the sequence of two or more SNPs determined from the statistical model further comprises setting the posterior probability from a hidden Markov Model to about zero if the sequence is not compatible with the plurality of reads.

15. A non-transitory computer-readable medium as recited in claim 14, wherein the Markov Model output a posterior probability of a set of N heterozygous SNPs given a previous set of N heterozygous SNPs.

16. A non-transitory computer-readable medium as recited in claim 15, wherein N is one.

17. A non-transitory computer-readable medium as recited in claim 15, wherein N is three.

18. A non-transitory computer-readable medium as recited in claim 10, wherein the second population is a subset of the first population.

19. A system comprising:
one or more processors;
a display device;
one or more computer-readable media; and
one or more sequences of instructions stored on the one or more computer readable media,
wherein execution of the one or more sequences of instructions by the one or more processors causes an apparatus to:
obtain genomic data for over 50,000 single nucleotide polymorphisms (SNPS) from a first population of individuals;
provide linkage disequilibrium of single nucleotide polymorphisms (SNPs) in the first population of individuals;
provide over one million reads of nucleotide bases in each of one or more individuals from a related second population of individuals who were or could have been members of the first population, based on sequencing of a sample from the one or more individuals;
select segment size so that number of distinct haplotypes in segment does not exceed threshold J to collapse the number of haplotypes per segment;
determine a haplotype included in the first population of individuals based on both the linkage disequilibrium and the plurality of reads by setting a posterior probability of a sequence of two or more SNPs determined from a statistical model for haplotype transitions per segment to a value compatible with the plurality of reads in at least one iteration of a forward backward algorithm; and
presenting, on the display device, data that indicates the haplotype included in the first population.

20. A system as recited in claim 19, wherein the one or more sequences of instructions executing on the one or more processors further cause the apparatus to determine the likely haplotype included in a chromosome of an individual based, at least in part, on the haplotype included in the first population and one or more reads of nucleotide bases for the individual.

21. A system as recited in claim 20, wherein determining the haplotype included in the chromosome of the individual further comprises determining a most likely assortment of alleles along the chromosome for the individual.

22. A system as recited in claim 19, wherein determining the plurality of reads of nucleotide bases in the one or more individuals further comprises determining the plurality of reads of nucleotide bases in the one or more individuals based on ultra-high throughput sequencing of the sample from the one or more individuals.

23. A system as recited in claim 19, wherein setting the posterior probability of the sequence of two or more SNPs determined from the statistical model further comprises setting the posterior probability from a hidden Markov Model to about zero if the sequence is not compatible with the plurality of reads.

24. A system as recited in claim 23, wherein the Markov Model output a posterior probability of a set of N heterozygous SNPs given a previous set of N heterozygous SNPs.

25. A system as recited in claim 24, wherein N is one.

26. A system as recited in claim 19, wherein the second population is a subset of the first population.

27. The method as recited in claim 1, further comprising, before providing the over one million reads of nucleotide bases, collecting the over one million reads of nucleotide bases for each of the one or more individuals in the second population.

* * * * *